United States Patent
Goldfain et al.

(10) Patent No.: US 7,364,297 B2
(45) Date of Patent: Apr. 29, 2008

(54) DIGITAL DOCUMENTING OPHTHALMOSCOPE

(75) Inventors: Ervin Goldfain, Syracuse, NY (US);
Jon Salvati, Skaneateles, NY (US);
David Fallat, Auburn, NY (US);
Marcia Wawro, Auburn, NY (US);
Michael McMahon, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 385 days.

(21) Appl. No.: 10/976,029

(22) Filed: Oct. 28, 2004

(65) Prior Publication Data

US 2005/0110949 A1    May 26, 2005

Related U.S. Application Data

(60) Provisional application No. 60/515,136, filed on Oct. 28, 2003.

(51) Int. Cl.
*A61B 3/10* (2006.01)
(52) U.S. Cl. .................. 351/206; 351/205; 351/218; 396/18; 606/4
(58) Field of Classification Search ............... 351/205, 351/206, 218; 396/18; 600/452; 606/4
See application file for complete search history.

(56) References Cited

U.S. PATENT DOCUMENTS

| | | |
|---|---|---|
| 3,586,424 A | 6/1971 | Schenk et al. |
| 3,614,214 A | 10/1971 | Cornsweet et al. |
| 3,638,641 A | 2/1972 | Abromavage et al. |
| 3,698,099 A | 10/1972 | Matsura et al. |
| 3,893,447 A | 7/1975 | Hochheimer et al. |
| 3,914,032 A | 10/1975 | Takano et al. |
| 3,915,564 A | 10/1975 | Urban |
| 3,925,793 A | 12/1975 | Matsumura et al. |
| 3,936,844 A | 2/1976 | Matsumura et al. |
| 3,944,341 A | 3/1976 | Pomerantzeff |
| 4,023,189 A | 5/1977 | Govignon |
| 4,026,638 A | 5/1977 | Govignon |
| 4,068,932 A | 1/1978 | Ohta et al. |
| 4,095,379 A | 6/1978 | Weintraub |
| 4,102,563 A | 7/1978 | Matsumura et al. |
| 4,106,078 A | 8/1978 | Inoue et al. |
| 4,135,791 A | 1/1979 | Govignon |
| 4,146,310 A | 3/1979 | Kohayakawa et al. |
| 4,149,787 A | 4/1979 | Kobayashi et al. |

(Continued)

FOREIGN PATENT DOCUMENTS

DE     19744131 A1    4/1998

(Continued)

OTHER PUBLICATIONS

U.S. Appl. No. 29/207233, filed Jun. 10, 2004, Fitch et al.

(Continued)

*Primary Examiner*—Ricky Mack
*Assistant Examiner*—Joseph Martinez

(57) ABSTRACT

The invention is an eye viewing device having an eyepiece at an observer end thereof and an imaging element at an observation port thereof. Light that is reflected from an imaged eye of a patient is provided to either or both of the eyepiece and the imaging element. A practitioner can view the imaged eye, and can sequentially image the same region of the imaged eye for recording, documentation, and/or analysis.

13 Claims, 20 Drawing Sheets

U.S. PATENT DOCUMENTS

| | | |
|---|---|---|
| 4,162,827 A | 7/1979 | Ito et al. |
| 4,176,920 A | 12/1979 | Ito et al. |
| 4,184,752 A | 1/1980 | Richards et al. |
| 4,187,014 A | 2/1980 | Kato et al. |
| 4,196,979 A | 4/1980 | Kohayakawa et al. |
| 4,198,144 A | 4/1980 | Matsumura et al. |
| 4,201,456 A | 5/1980 | Wolbarsht |
| 4,227,780 A | 10/1980 | Ohta et al. |
| 4,235,540 A | 11/1980 | Hanamura et al. |
| 4,238,142 A * | 12/1980 | Richards et al. ............ 351/206 |
| 4,247,176 A | 1/1981 | Ito et al. |
| 4,248,505 A | 2/1981 | Muchel et al. |
| 4,248,506 A | 2/1981 | Takahashi et al. |
| 4,249,802 A | 2/1981 | Muchel et al. |
| 4,249,825 A | 2/1981 | Shapiro |
| 4,251,139 A | 2/1981 | Matsumura et al. |
| 4,252,420 A | 2/1981 | Kohayakawa et al. |
| 4,253,743 A | 3/1981 | Matsumura et al. |
| 4,253,744 A | 3/1981 | Sawa et al. |
| 4,257,688 A | 3/1981 | Matsumura et al. |
| 4,257,691 A | 3/1981 | Brooks |
| 4,264,153 A | 4/1981 | Ito et al. |
| 4,265,518 A | 5/1981 | Matsumura et al. |
| 4,265,519 A | 5/1981 | Pomerantzeff |
| 4,266,861 A | 5/1981 | Sawa et al. |
| 4,279,478 A | 7/1981 | Matsumura et al. |
| 4,283,124 A | 8/1981 | Matsumura et al. |
| 4,318,585 A | 3/1982 | Matsumura et al. |
| 4,329,025 A | 5/1982 | Nishimura et al. |
| 4,331,132 A | 5/1982 | Mukasa et al. |
| 4,365,872 A | 12/1982 | Nunokawa et al. |
| 4,378,147 A | 3/1983 | Fujita et al. |
| 4,400,070 A | 8/1983 | Isono et al. |
| 4,405,215 A | 9/1983 | Sano et al. |
| 4,412,728 A | 11/1983 | Sakane et al. |
| 4,422,735 A | 12/1983 | Shimizu et al. |
| 4,422,736 A | 12/1983 | Nunokawa et al. |
| 4,423,932 A | 1/1984 | Takahashi et al. |
| 4,435,051 A | 3/1984 | Nunokawa et al. |
| 4,436,388 A | 3/1984 | Takahashi et al. |
| 4,436,389 A | 3/1984 | Sano et al. |
| 4,439,023 A | 3/1984 | Iba et al. |
| 4,439,024 A | 3/1984 | Ito et al. |
| 4,449,798 A | 5/1984 | Nohda et al. |
| 4,453,808 A | 6/1984 | Takahashi et al. |
| 4,464,608 A | 8/1984 | Pilley |
| 4,469,416 A | 9/1984 | Isono et al. |
| 4,485,820 A | 12/1984 | Flower |
| 4,502,766 A | 3/1985 | Ito et al. |
| 4,511,227 A | 4/1985 | Nunokawa et al. |
| 4,526,450 A | 7/1985 | Suzuki et al. |
| 4,529,280 A | 7/1985 | Nohda et al. |
| 4,558,932 A | 12/1985 | Nunokawa et al. |
| 4,572,627 A | 2/1986 | Madate et al. |
| 4,580,885 A | 4/1986 | Takahashi et al. |
| 4,591,249 A | 5/1986 | Takahashi et al. |
| 4,613,218 A | 9/1986 | Machida et al. |
| 4,666,268 A | 5/1987 | Ito et al. |
| 4,673,264 A | 6/1987 | Takahashi et al. |
| 4,679,919 A | 7/1987 | Itoh et al. |
| 4,682,866 A | 7/1987 | Volk |
| 4,690,525 A | 9/1987 | Kobayashi et al. |
| 4,712,894 A | 12/1987 | Nunokawa et al. |
| 4,715,703 A | 12/1987 | Cornsweet et al. |
| 4,715,704 A | 12/1987 | Biber et al. |
| 4,717,952 A | 1/1988 | Kohayakawa et al. |
| 4,721,378 A | 1/1988 | Volk |
| 4,732,466 A | 3/1988 | Humphrey |
| 4,755,043 A | 7/1988 | Carter |
| 4,755,044 A | 7/1988 | Thorn |
| 4,756,613 A | 7/1988 | Okashita et al. |
| 4,776,464 A | 10/1988 | Miller et al. |
| 4,799,783 A | 1/1989 | Takahashi et al. |
| 4,812,033 A | 3/1989 | Ishikawa et al. |
| 4,824,238 A | 4/1989 | Feldman et al. |
| 4,834,526 A | 5/1989 | Nunokawa et al. |
| 4,856,872 A | 8/1989 | Spitznas et al. |
| 4,856,890 A | 8/1989 | Itoh et al. |
| 4,856,891 A | 8/1989 | Pflibsen et al. |
| 4,867,554 A | 9/1989 | Matsumura et al. |
| 4,927,260 A | 5/1990 | Gordon |
| 4,989,023 A | 1/1991 | Sakurai et al. |
| 4,991,584 A | 2/1991 | Kobayashi et al. |
| 4,998,533 A | 3/1991 | Winkelman |
| 5,037,194 A | 8/1991 | Kohayakawa et al. |
| 5,071,245 A | 12/1991 | Fukuma et al. |
| 5,138,140 A | 8/1992 | Siemiatkowski et al. |
| 5,140,352 A | 8/1992 | Moore et al. |
| 5,140,458 A | 8/1992 | Takagi et al. |
| 5,141,303 A | 8/1992 | Yamamoto et al. |
| 5,177,512 A | 1/1993 | Abe et al. |
| 5,181,055 A | 1/1993 | Sano et al. |
| 5,187,506 A | 2/1993 | Carter |
| 5,189,556 A | 2/1993 | Ohtsuka et al. |
| 5,214,454 A | 5/1993 | Sano et al. |
| 5,233,372 A | 8/1993 | Matsumoto et al. |
| 5,237,350 A | 8/1993 | Sano et al. |
| 5,237,356 A | 8/1993 | Ohtsuka et al. |
| 5,239,984 A | 8/1993 | Cane et al. |
| 5,247,318 A | 9/1993 | Suzuki et al. |
| 5,255,025 A | 10/1993 | Volk |
| 5,255,026 A | 10/1993 | Arai et al. |
| 5,270,747 A | 12/1993 | Kitajima et al. |
| 5,270,749 A | 12/1993 | Okumura et al. |
| 5,270,924 A | 12/1993 | Hideshima et al. |
| 5,287,129 A | 2/1994 | Sano et al. |
| 5,291,231 A | 3/1994 | Hideshima et al. |
| 5,300,964 A | 4/1994 | Kobayashi et al. |
| 5,329,322 A * | 7/1994 | Yancey ...................... 351/211 |
| 5,374,967 A | 12/1994 | Hideshima et al. |
| 5,408,264 A | 4/1995 | Kurata et al. |
| 5,420,650 A | 5/1995 | Kohayakawa et al. |
| 5,424,789 A | 6/1995 | Volk |
| 5,446,509 A | 8/1995 | Okinishi et al. |
| 5,500,697 A | 3/1996 | Fujieda et al. |
| 5,523,808 A | 6/1996 | Kohayakawa et al. |
| 5,528,323 A | 6/1996 | Fujieda et al. |
| 5,530,493 A | 6/1996 | Suzuki et al. |
| 5,539,517 A | 7/1996 | Cabib et al. |
| 5,543,865 A | 8/1996 | Nanjo et al. |
| 5,557,321 A | 9/1996 | Kohayakawa et al. |
| 5,565,938 A | 10/1996 | Hanamura et al. |
| 5,572,266 A | 11/1996 | Ohtsuka et al. |
| 5,576,780 A | 11/1996 | Yancey |
| 5,579,063 A | 11/1996 | Magnante et al. |
| 5,599,276 A | 2/1997 | Hauptli et al. |
| 5,607,187 A | 3/1997 | Salive et al. |
| 5,617,156 A | 4/1997 | Sano et al. |
| 5,633,694 A | 5/1997 | Mihashi et al. |
| 5,642,442 A | 6/1997 | Morton et al. |
| 5,668,621 A | 9/1997 | Nanjo et al. |
| 5,695,492 A | 12/1997 | Brown |
| 5,713,047 A | 1/1998 | Kohayakawa et al. |
| 5,722,762 A | 3/1998 | Soll |
| 5,742,374 A | 4/1998 | Nanjo et al. |
| 5,745,163 A | 4/1998 | Nakamura et al. |
| 5,751,395 A | 5/1998 | Thall |
| 5,757,463 A | 5/1998 | Kohayakawa et al. |
| 5,762,605 A | 6/1998 | Cane et al. |
| 5,764,341 A | 6/1998 | Fujieda et al. |
| 5,857,029 A | 1/1999 | Patel |
| 5,880,813 A | 3/1999 | Thall |
| 5,914,771 A | 6/1999 | Biber et al. |
| 5,919,130 A | 7/1999 | Monroe et al. |

| | | |
|---|---|---|
| 5,993,001 A | 11/1999 | Bursell et al. |
| 5,993,002 A | 11/1999 | Steinhuber et al. |
| 5,995,759 A | 11/1999 | Kohayakawa |
| 6,007,996 A | 12/1999 | McNamara et al. |
| 6,008,781 A | 12/1999 | Furness, III et al. |
| 6,019,286 A | 2/2000 | Li et al. |
| 6,030,080 A | 2/2000 | Ohman et al. |
| 6,065,837 A | 5/2000 | Goldfain et al. |
| 6,075,599 A | 6/2000 | Milman et al. |
| 6,082,859 A | 7/2000 | Okashita et al. |
| 6,094,509 A | 7/2000 | Zheng et al. |
| 6,115,513 A | 9/2000 | Miyazaki et al. |
| 6,116,736 A | 9/2000 | Stark et al. |
| 6,122,410 A | 9/2000 | Zheng et al. |
| 6,139,151 A | 10/2000 | Ueno et al. |
| 6,142,629 A | 11/2000 | Adel et al. |
| 6,152,565 A | 11/2000 | Liu et al. |
| 6,158,864 A | 12/2000 | Masuda et al. |
| 6,165,734 A | 12/2000 | Garini et al. |
| 6,193,371 B1 | 2/2001 | Snook |
| 6,196,686 B1 | 3/2001 | Reiner et al. |
| 6,198,532 B1 | 3/2001 | Cabib et al. |
| 6,244,710 B1 | 6/2001 | Ogawa et al. |
| 6,273,565 B1 | 8/2001 | Matsumoto |
| 6,296,358 B1 | 10/2001 | Cornsweet et al. |
| 6,325,511 B1 | 12/2001 | Mizuochi et al. |
| 6,327,375 B1 | 12/2001 | Matsumoto et al. |
| 6,364,484 B2 | 4/2002 | Yamada et al. |
| 6,390,625 B1 | 5/2002 | Slawson et al. |
| 6,404,985 B1 | 6/2002 | Ohtsuka et al. |
| 6,409,341 B1 | 6/2002 | Goldfain et al. |
| 6,456,787 B1 | 9/2002 | Matsumoto et al. |
| 6,488,377 B2 | 12/2002 | Matsumoto et al. |
| 6,511,420 B1 | 1/2003 | Farrell et al. |
| 6,527,390 B2 | 3/2003 | Goldfain et al. |
| 6,546,198 B2 | 4/2003 | Ohtsuka et al. |
| 6,550,916 B1 | 4/2003 | Sekiguchi et al. |
| 6,574,432 B2 | 6/2003 | Nanjyo et al. |
| 6,575,571 B2 | 6/2003 | Shibata et al. |
| 6,585,374 B2 | 7/2003 | Matsumoto et al. |
| 6,636,696 B2 | 10/2003 | Saito et al. |
| 6,637,882 B1 | 10/2003 | Goldfain et al. |
| 6,644,809 B2 | 11/2003 | Ogawa et al. |
| 6,654,553 B2 | 11/2003 | Shibata et al. |
| 6,669,339 B2 | 12/2003 | Nanjyo et al. |
| 6,692,125 B2 | 2/2004 | Matsumoto et al. |
| 6,729,727 B2 | 5/2004 | Nanjo et al. |
| 6,749,301 B2 | 6/2004 | Silverbrook et al. |
| 6,755,526 B2 | 6/2004 | Shibata et al. |
| D493,528 S | 7/2004 | Roberts et al. |
| D493,887 S | 8/2004 | Roberts et al. |
| 6,773,109 B2 | 8/2004 | Ichikawa et al. |
| 6,779,890 B2 | 8/2004 | Matsumoto et al. |
| 6,830,347 B2 | 12/2004 | Slawson et al. |
| 6,832,835 B2 | 12/2004 | Matsumoto et al. |
| 6,939,006 B2 | 9/2005 | Goldfain et al. |
| 6,968,127 B2 | 11/2005 | Nanjyo et al. |
| 2002/0097379 A1 | 7/2002 | Goldfain et al. |
| 2003/0071893 A1 | 4/2003 | Miller et al. |
| 2003/0157464 A1 | 8/2003 | Tanassi et al. |
| 2003/0208125 A1 | 11/2003 | Watkins |

FOREIGN PATENT DOCUMENTS

| | | |
|---|---|---|
| EP | 1152687 | 11/2001 |
| JP | 50147928 | 11/1975 |
| JP | 51049024 | 4/1976 |
| JP | 52025494 | 2/1977 |
| JP | 53126792 | 11/1978 |
| JP | 54006393 | 1/1979 |
| JP | 55045216 B | 11/1980 |
| JP | 57148929 A | 9/1982 |
| JP | 60210240 A | 10/1985 |
| JP | 61269108 | 11/1986 |
| JP | 62500914 T | 4/1987 |
| JP | 62220916 A | 9/1987 |
| JP | 01-150905 | 10/1989 |
| JP | 6285026 | 10/1994 |
| JP | 07 077658 | 3/1995 |
| JP | 3017433 U | 8/1995 |
| JP | 8317907 A | 12/1996 |
| JP | 11 089798 A | 4/1999 |
| WO | WO 0030527 A1 | 6/2000 |
| WO | WO 01/89374 | 11/2001 |
| WO | WO 02/087427 | 11/2002 |
| WO | WO-2005/020804 A1 | 3/2005 |

OTHER PUBLICATIONS www.DELPHION.COM, Internet Search of US20020097379A1: Eye Viewing Device Comprising Eyepiece and Video Capture Optics, "Patent Family" Internet Search Dated Jun. 23, 2007 (3 pages). Reference summarizes data.
Express Abandonment Under 37 CFR 1.138, dated Jan. 12, 2005, submitted in U.S. Appl. No. 10/671,645, filed Sep. 25, 2003. Also, an Express Abandonment Remarks Amendment.
JP Patent Application 2000-583418 Notice of Grounds for Rejection in the English language.
Australian Government, IP Australia, Examiner's First Report on Patent Application No. 2001263366 by Welch Allyn, Inc. dated Dec. 9, 2004, 2 pages.
Australian Government, IP Australia, Examiner's Second Report on Patent Application No. 2001263366 by Welch Allyn, Inc. dated Dec. 19, 2005, 2 pages.
Japanese Patent Office, Examiner's Mailing No. 036153, Notice of Grounds for Rejection dated Jan. 31, 2006 for Japanese Patent Application No. 2000-583418, 3 pages.
Canadian Intellectual Property Office, Requisition by Examiner dated Feb. 28, 2006 for Canada Application No. 2,352,148 by Welch Allyn, Inc., 4 pages.
Australian Government, IP Australia, Examiner's Third Report on Patent Application No. 2001263366 by Welch Allyn, Inc. dated Mar. 17, 2006, 2 pages.

* cited by examiner

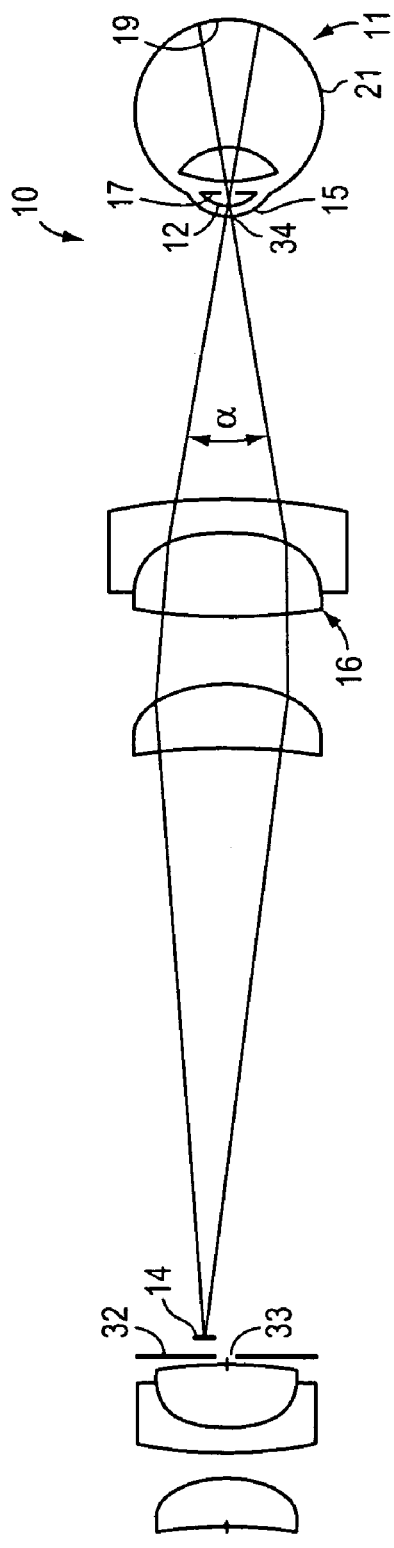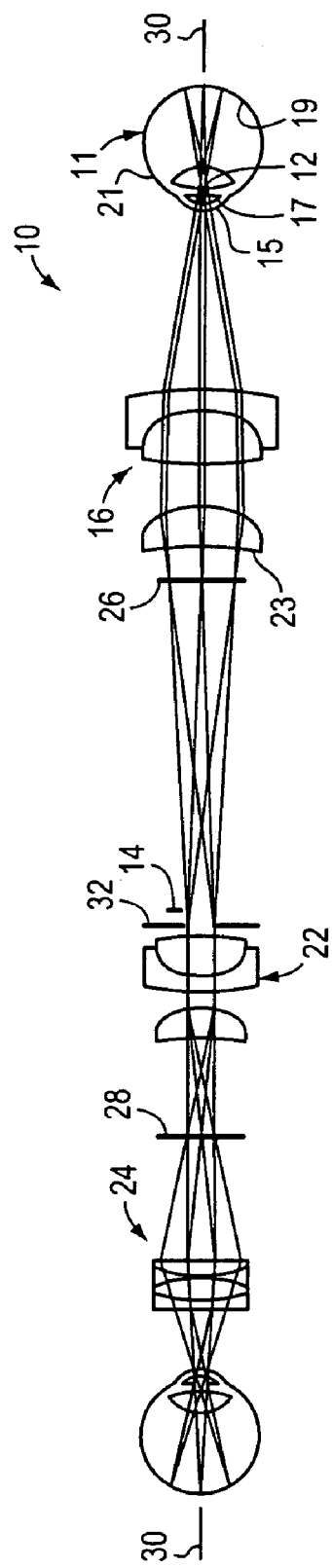
FIG. 1A
FIG. 1B

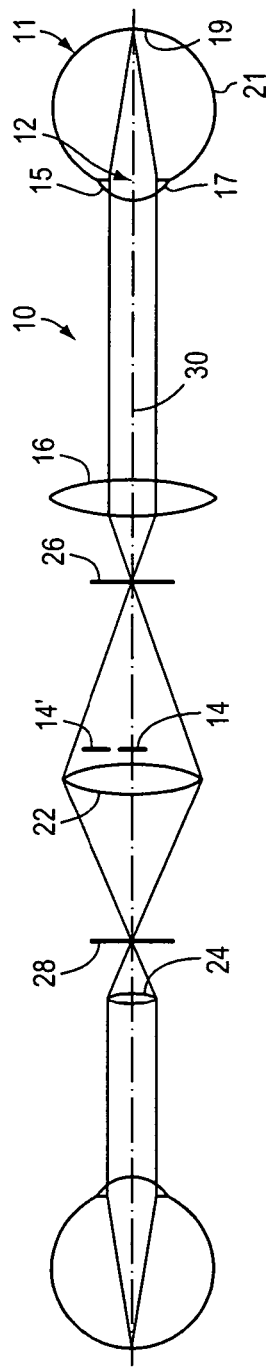
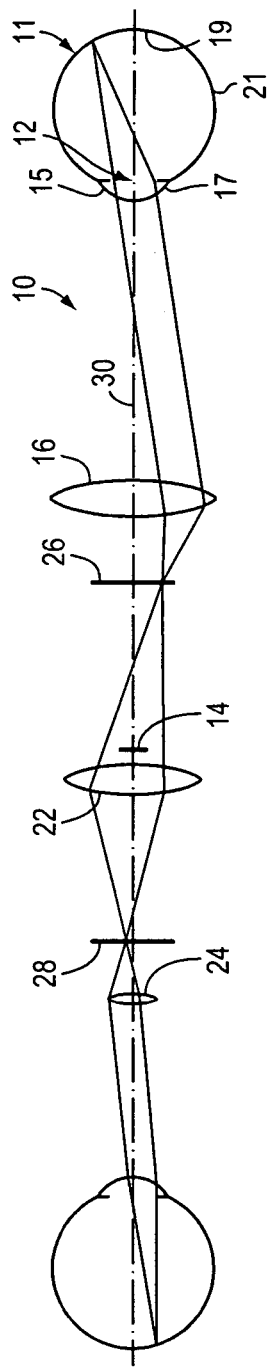
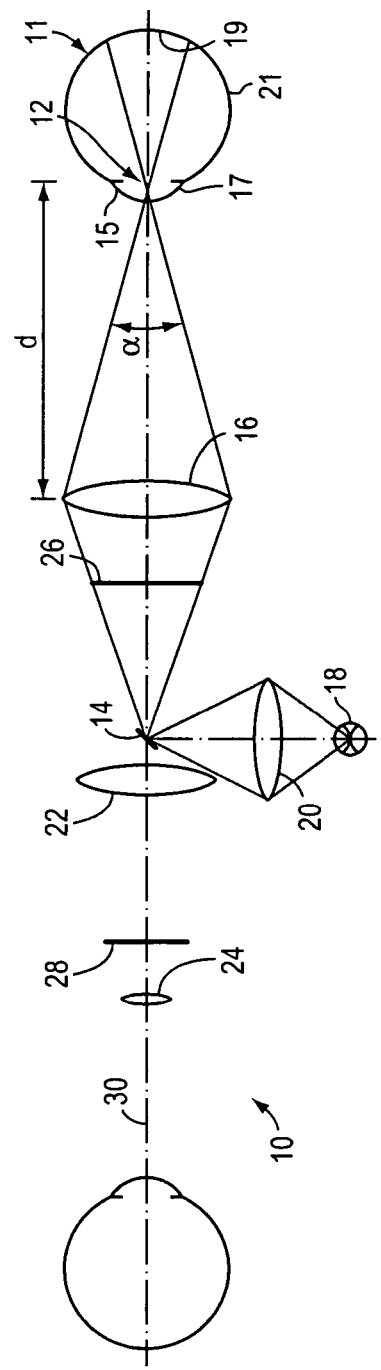
FIG. 3A
FIG. 3B
FIG. 3C

DIGITAL DOCUMENTING OPHTHALMOSCOPE

CROSS-REFERENCE TO RELATED APPLICATIONS

This application claims priority to and the benefit of now abandoned U.S. Provisional Patent Application Ser. No. 60/515,136, filed Oct. 28, 2003, which application is incorporated herein by reference in its entirety. This application is related to U.S. patent application Ser. No. 09/862,636 entitled "Eye Viewing Device Comprising Eyepiece and Video Capture Optics" filed May 22, 2001, which is a Continuation-in-part of U.S. patent application Ser. No. 09/783,481 entitled "Eye Viewing Device for Retinal Viewing Through Undilated Pupil" filed Feb. 14, 2001, which is a Continuation-in-part of U.S. patent application Ser. No. 09/444,161 entitled "Eye Viewing Device for Retinal Viewing Through Undilated Pupil" filed Nov. 22, 1999, which is a Continuation-in-part of U.S. patent application Ser. No. 09/198,545 entitled "Ophthalmoscope Comprising Defocused Light Source" filed Nov. 24, 1998, which issued May 23, 2000 as U.S. Pat. No. 6,065,837. Each of the above-identified applications is incorporated herein by reference in its entirety.

FIELD OF THE INVENTION

The invention relates generally to medical diagnostic instruments, and specifically to an eye viewing device for use in retinal viewing.

BACKGROUND OF THE INVENTION

Commercially available eye viewing devices for use in retinal viewing have been observed to exhibit numerous limitations.

According to an ophthalmoscope design, a beam splitter is provided in the optical viewing path which directs illumination light rays into an eye, and simultaneously allows receive imaging light rays to pass therethrough. The substantial light losses inherent with this design requires that a large, high powered light source be incorporated in the device for the device to satisfactorily illuminate a retina. High powered light sources, in general, are difficult to package, consume excessive amounts of electrical input power, and produce large amounts of heat and unwanted light such as glare. High powered light sources also have large filaments, typically larger than the diameter of an undilated pupil. This makes indirect ophthalmoscopes especially susceptible to glare problems attributable to incident light rays being reflected from outer eye structures such as the iris, cornea and sclera. Additionally, because there is a limit to the level of illumination which is safe to introduce into they eye, high powered illumination systems never fully compensate for the losses introduced by a beamsplitter.

Cameras for use in retinal viewing, such as fundus cameras, provide high quality imaging. However, retinal viewing cameras, in general, are expensive, typically require pupil dilation for retinal viewing, and typically require operation by a highly skilled and trained camera operator and these cameras are also large, bulky, and consume excessive space. Because present retinal viewing cameras are fixed position cameras, they require that a a patient move into a certain position relative to the camera for an operative position to be achieved. Further, they frequently illuminate with infrared illumination only during "aiming" which makes the views during aiming unsuitable for diagnosis.

There is a need for a compact, lower input power eye hand-held viewing device which provides appropriate retinal illumination, which facilitates wide field retinal viewing without requiring pupil dilation, and which can be adapted for use in producing both a suitable view for diagnosis and the capability of capturing images corresponding to eye structures.

SUMMARY OF THE INVENTION

According to its major aspects and broadly stated, the present invention is a low input power, low cost eye viewing device for use in viewing a retina and for obtaining electronic images thereof.

The digital documenting ophthalmoscope comprises an illumination module for providing continuous, convergent illumination; an optical module configured to direct at least a portion of the illumination to an eye and to communicate return illumination from the eye through an undilated pupil of the eye, the at least a portion of the illumination directed toward the eye having an intensity below a safety limit, the optical module comprising a Maxwellian view system; a viewing module having an eyepiece configured to provide a true color live view to an operator of at least a portion of the eye using the return illumination; an electronic imager module having an imager for capturing an image of at least a portion of the eye using the return illumination; and a mirror having a first state to provide the true color live view of at least a portion of the eye and a second state to provide the image of at least a portion of the eye.

In one embodiment, the digital documenting ophthalmoscope further comprises an illumination control apparatus configured to direct the return illumination from the eye in part to the viewing module and in part to the electronic imager module. In one embodiment, the illumination control apparatus is configured to control in serial temporal fashion the return illumination directed in part to the viewing module and in part to the electronic imager module, such that direct viewing occurs during a first time interval and electronic imaging occurs during a second time interval, wherein the first and second time intervals do not substantially overlap. In one embodiment, the illumination control apparatus is a selected one of a mirror and a shutter. In one embodiment, the mirror is a selected one of a movable mirror and an electronically controllable mirror. In one embodiment, an integration time of the electronic imager is adjustable. In one embodiment, the integration time interval of the electronic imager is adjusted to be different than that of a viewing time interval.

In one embodiment, the digital documenting ophthalmoscope further comprises a dot plate glare removal apparatus. In one embodiment, the digital documenting ophthalmoscope further comprises glare removal apparatus comprising a polarizer and a dot plate.

In one embodiment, a field of view of at least 10 degrees is accessible for a selected one of a true color live view and an electronic image. In one embodiment, at least one of the illumination module and the optical module comprise a reconfigurable illumination system wherein an illumination angle is adjustable.

In another aspect, the invention features a method of obtaining information about at least a portion of an eye of a patient. The method comprises the steps of providing a hand held digital documenting ophthalmoscope. The hand held digital documenting ophthalmoscope comprises an illumination module for providing continuous, convergent illumination; an optical module configured to direct at least a portion of the illumination to an eye and to communicate return illumination from the eye through an undilated pupil of the eye, the at least the portion of the illumination directed toward the eye having an intensity below a safety limit, the optical module comprising a Maxwellian view system; a viewing module having an eyepiece configured to provide a live view by an operator of at least a portion of the eye using the return illumination; an electronic imager module having an imager for capturing an image of at least a portion of the eye using the return illumination; and a mirror having a first state to provide the live view of at least a portion of the eye and a second state to provide the image of at least a portion of the eye. The live view is a true color live view suitable for diagnosis. The method also includes the steps of illuminating at least a portion of the eye with illumination from the illumination module, the illumination passing through the optical module in at least one direction; controlling the state of the mirror; and depending on the state of the mirror, providing a selected one of a true color live view of at least a portion of the eye and an image of at least a portion of the eye; whereby information about at least a portion of the eye is obtained.

In one embodiment, the method further comprises the step of directing the return illumination from the eye in part to the viewing module and in part to the electronic imager module. In one embodiment, the step of directing the return illumination from the eye in part to the viewing module and in part to the electronic imager module comprises providing a direct view during a first time interval and providing electronic imaging during a second time interval, wherein the first and second time intervals do not substantially overlap.

In one embodiment, the method further comprises a step of adjusting an integration time of the electronic imager. In one embodiment, the method further comprises the step of removing glare from a selected one of the true color live view of the portion of the eye and the image of the portion of the eye.

In yet another aspect, the invention relates to a method of assessing a condition of an eye in a single interrogation of the eye. The method comprises the steps of viewing the eye in a true color live view by an operator; and capturing an image of the eye in an imager.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views. One or more embodiments of the invention will now be described by way of example only, with reference to the accompanying figures, wherein:

FIG. 1A is a functional schematic diagram of an eye viewing device according to the invention showing illumination light rays for illustrating operation of an illumination system according to the invention;

FIG. 1B is a functional schematic diagram of an eye viewing device according to the invention showing receive optical light rays which illustrate operation of the device's imaging system;

FIG. 3A is a functional schematic diagram of an embodiment of the invention showing light rays from an on-axis object illustrating operation of an imaging system having a defocused mirror;

FIG. 3B is a functional schematic diagram of an embodiment of the invention showing light rays from an off-axis object illustrating operation of an imaging system having a defocused mirror;

FIG. 3C is a functional schematic diagram of an embodiment of the invention showing illumination light rays which illustrate operation of an illumination system having an on-axis light source;

FIGS. 6A-6K are physical schematic diagrams illustrating various features which may be incorporated in certain specific embodiments of the invention;

DETAILED DESCRIPTION OF THE INVENTION

An exemplary embodiment of an eye viewing device according to the invention is described with reference to FIGS. 1A-1E. Eye viewing device 10 includes an illumination system, the operation of which is described mainly with reference to FIG. 1A, and an imaging system, the operation of which is described mainly with reference to FIG. 1B.

The device of FIGS. 1A-1E is especially well suited for use in viewing a retina through an undilated pupil. Small diameter undilated pupils present numerous challenges to viewing retinal images. Small diameter undilated pupils tend to inhibit the transmission of both incident light directed toward a retina and reflected light corresponding to a retinal image. Furthermore, light that is directed into a pupil and that is blocked from entry into a pupil by highly reflective surfaces of outer eye structures such as the iris and sclera tends to be reflected into a viewing system as glare. As will be explained herein below, the device of FIGS. 1A-1E includes features which operate in combination to overcome the numerous challenges to viewing a retinal image through an undilated pupil. In one aspect, the device of FIGS. 1A-1E includes the combination of a converging light source illumination system and an aperture stop. The converging light source illumination system operates to direct a substantial amount of light through a small diameter opening while the aperture stop operates to block glare attributable to light rays being reflected from outer eye structures.

Figure 1C:
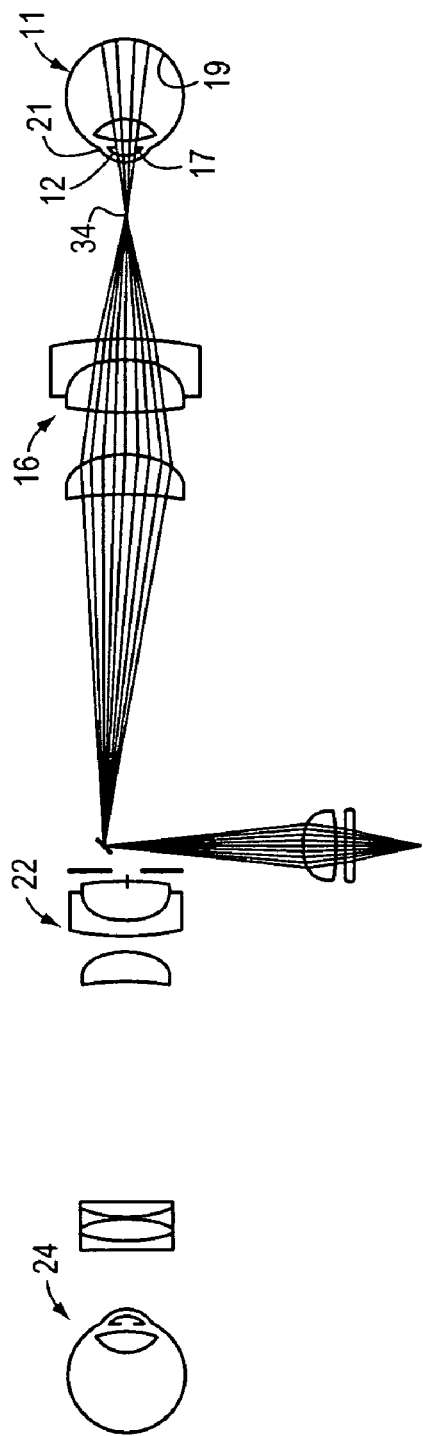
FIG. 1C is a functional schematic diagram of an eye viewing device according to the invention showing incident illumination light rays when the device is at a distance away from an operative position.

As best seen by FIG. 1A, the illumination system operates to generate illumination light rays that converge at an apex 34 and diverge thereafter. An eye viewing device having a converging light ray illumination system is positioned in an operative position relative to a patient when substantially a maximum amount of incident light enters eye 11 through pupil 12. In the device of FIG. 1A-1E, an operative position is achieved when apex 34 of the cone of light generated by the illumination system is positioned at about a pupil 12 of a patient. With a converging light ray illumination system, a substantial amount of illumination light enters a pupil of small diameter and at the same time illuminates a wide retinal field. A converging light ray illumination system can be provided by the combination of a light source 14 and objective lens 16 positioned forward of the light source 14 for converging light rays emanating from the source 14. With a converging light source illumination system, a much higher percentage of incident light rays enter the pupil 12 to illuminate the retina 19 than are reflected off outer eye structures 17 and 21. Because there is little wasted incident light, a converging light ray illumination system reduces the electrical input power consumption of the illumination system. Because a relatively smaller amount of incident light reflects off outer eye structures such as iris 17 and sclera 21, there is less unwanted light received by the imaging system.

Figure 2A:
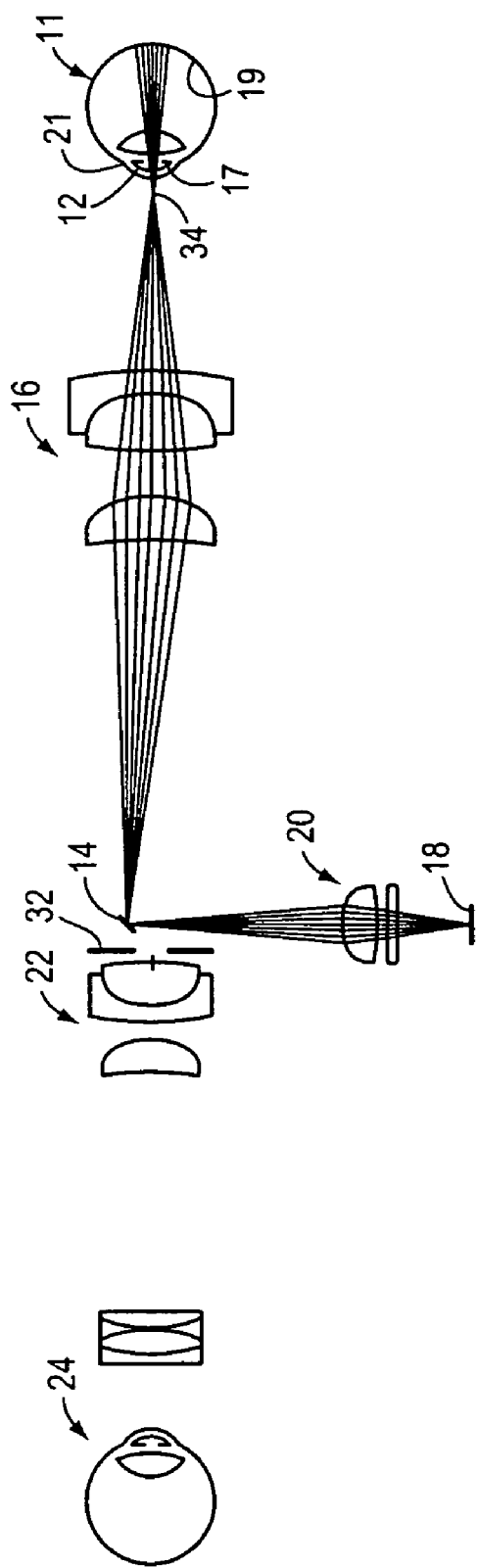
FIG. 2A is a functional schematic diagram showing incident light rays of an illumination system which may be incorporated in embodiments of the invention.

Light source 14 can be a light generating light source, such as a filament-based lamp, an arc lamp, a fiber optic light source or a solid state light source. However, with presently available technology, light generating light sources are sufficiently large that they introduce packaging problems. Therefore, a preferred light source for the eye viewing device is the light source described with reference to FIG. 2A. In the embodiment of FIG. 2A, light source 14 is provided by a reflective element such as a mirror, which operates in association with a light-generating light source 18, such as a lamp, and a condenser lens 20 that converges light from light source 18 onto mirror 14.

Aspects of the imaging system of the device will now be described with reference mainly to FIG. 1B. The imaging system of the device includes objective lens 16, imaging lens 22, and an eyepiece lens 24. A retinal image focal plane 26 is produced intermediate objective lens 16 and imaging lens 22, while an eyepiece focal plane 28 is produced intermediate imaging lens 22 and eyepiece lens 24. The imaging system further includes an imaging axis 30 on which lenses 16, 22, and 24 are substantially centered. In all references herein, the term "lens" can refer to a single optical element or a plurality of optical elements functioning together, while an operative position has been defined herein as the position at which substantially a maximum amount of incident light rays enter eye 11 through pupil 12. An operative position can also be defined as the position at which a patient's pupil is conjugate to aperture stop 32.

The retinal image light rays crossing retinal focal plane 26 consist of light rays that enter eye 11 through pupil 12 and which are reflected from retina 19 through pupil 12. Since small undilated pupils tend to inhibit the transmission of both incident light into an eye and reflected retinal image light out of the eye, retinal images viewed through undilated pupils are readily obscured by glare (which is especially prevalent when retinas are viewed through undilated pupils since incident light is more likely to be reflected from highly reflective outer eye structures). In addition to glare attributable to light being reflected from outer eye structures, retinal images can be obscured by glare attributable to other sources such as light that is reflected from a patient's cornea (corneal glare) and light that is reflected from a component of the eye viewing device such as a lens of the device (internal glare).

To the end that the device is well adapted for viewing retinal images through an undilated pupil, device 10 preferably includes features which operate to reduce such glare, and in so doing reduce the percentage of received light rays not corresponding to a retinal image relative to the percentage of received light rays corresponding to a retinal image.

One feature, which operates to reduce the percentage of light rays not corresponding to the retinal image, is the feature of converging light illumination, described above. In a converging light illumination system, a relatively high percentage of light enters eye 11 through pupil 12, and a relatively low percentage of light is reflected from outer eye structures 17 and 21 as seen in FIG. 1A. Other features which may be incorporated to increase the percentage of retinal image forming received light relative to unwanted light are described hereinbelow.

In the device of FIG. 1B, an aperture stop 32 is positioned forward of imaging lens 22 to block unwanted light. Aperture stop 32 should be positioned substantially coaxially with imaging axis 30 and substantially conjugate to a patient's pupil 12 when in an operative position in relation to device 10. Positioning of aperture stop 32 substantially coaxial with imaging axis 30 encourages substantially a maximum amount of useful received (or returned) imaging light to be admitted through imaging lens 22 without also admitting glare light that originates radially outside the patient's pupil 12. By positioning aperture stop 32 so that it is substantially conjugate to a pupil, aperture stop 32 operates to block light reflected from outer eye structures 17 and 21. Because the apex 34 of the cone of light generated by illumination system is substantially conjugate to a patient's pupil for positioning the device in an operative position, and because the preferred position of aperture stop is also one that is conjugate to the pupil, then the preferred position of aperture stop 32 in a device made in accordance with FIGS. 1A-1E can be described as one that is substantially conjugate to the apex of the cone of light generated by the illumination system.

For optimal blocking of unwanted received light, aperture 33 of aperture stop 32 should be sized in accordance with the diameter of the pupil through which a retina is viewed. The diameter of an undilated pupil is about 2 mm. Accordingly, for optimally configuring device 10 for viewing a retina through an undilated pupil, aperture 33 should be sized to correspond to a patient pupil diameter of about 2 mm. The resulting diameter of aperture 33 is determined by multiplying the pupil diameter by the magnification of the pupil in the plane of the aperture stop 32. This same principle can be applied to optimize the instrument design for other pupil sizes, larger and smaller.

Figure 1D:
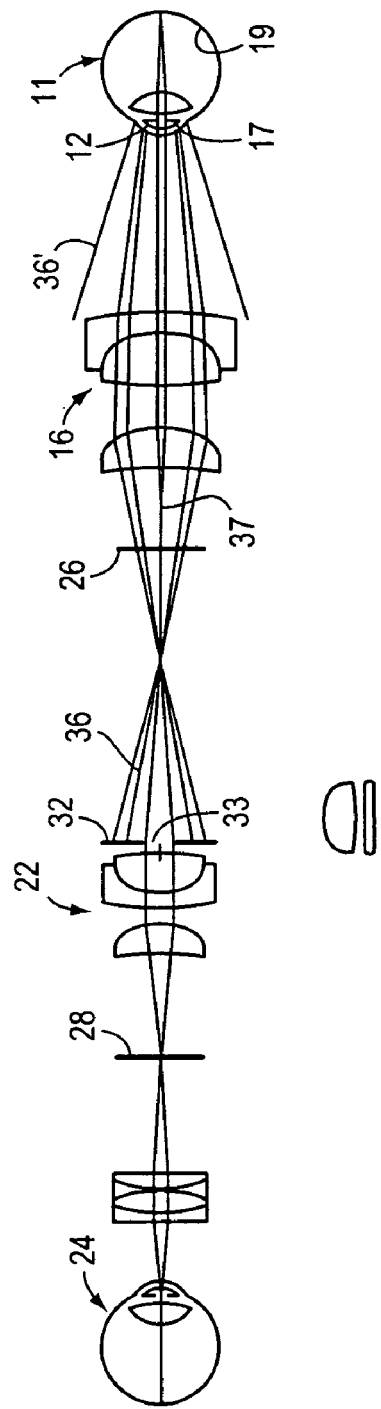
FIG. 1D is a functional schematic diagram of the eye viewing device of FIG. 1C showing receive optical light rays when the device is at a distance away from an operative position.

In addition to reducing glare and improving image quality when device 10 is in an operative position, aperture stop 32 reduces glare and improves image quality prior to the device being moved into an operative position. FIGS. 1C and 1D illustrate illumination light rays exiting the device and reflecting off the eye as they are received in a viewing system of device 10 during entry of the device into an eye (during the process of moving the device into an operative position). FIG. 1C illustrates incident light rays generated by device 10 when the device is at a distance away from an operative position, while FIG. 1D illustrates received reflected light rays of a device positioned at the same distance away from an operative position as is shown in FIG. 1C. It is seen that when the device is away from an operative position, then light rays generated by the illumination system strike eye 11 in a diverged state (apex 34 of the cone of light is positioned forward of pupil 12). Thus, a relatively small percentage of incident rays enter an eye through pupil 12 and a relatively high percentage light rays are reflected from the highly reflective outer surfaces of eye structures such as iris 17 and sclera 21. Light rays reflected from outer eye structures 17 and 21 tend to be reflected at an angle with respect to imaging axis 30. The curved surface of eye 11 assures that reflected light rays are reflected at an angle with respect to axis 30. When device 10 is a substantial distance away from an operative position many light rays reflected from eye 11 during entry of the device are reflected out of the viewing system entirely as is indicated by rays 36. The majority of light rays that are received in the viewing system are blocked by aperture stop 32 as is indicated by rays 36. Only a small percentage of light rays such as rays 37 pass through aperture 33. Light rays that pass through aperture 33 consist of rays that originated as incident light rays directed substantially along axis 30 and that passed through pupil 12 to retina 19. Thus, during entry of device 10 into eye 11, it can be seen that aperture stop 32 tends to block unwanted light and to pass light corresponding to a retinal image.

It will be seen that without aperture stop 32, a substantial majority of light rays transmitted to eyepiece focal plane 28 during entry would be light rays reflected from outer eye structures 17 and 21. Thus, the image received at eyepiece focal plane 28 would be heavily obscured by glare. With aperture stop 32 the substantial majority of light rays received at eyepiece focal plane correspond to retina 19. During entry into the eye, the user will see a small field image of the retina, known as the "red reflex" which helps an operator move the device into an operative position without significant glare. An operative position can easily be achieved by maintaining the retinal image spot near the center of eyepiece focal plane 28 and moving the device toward an eye 11.

Additional glare or unwanted light reducing features may be incorporated in the device. As is shown in FIGS. 1A-1E, light source 14 may be positioned just forward of aperture stop 32 outside of the boundary between received and blocked light and off-axis with respect to imaging axis 30 of device 10. Positioning light source forward of aperture stop 32, outside of the boundary between received and blocked light defined by aperture 33, assures that light source 14 has no obscuring effect on the viewed image and assures maximum image brightness in the user's eye. Positioning light source 14 off-axis also reduces both internal and corneal glare. By positioning light source off-axis, incident light that is reflected off of lens 16 or off of cornea 15 is directed at an angle with respect to axis 30 and, therefore, away from the optical receive path.

Figure 1E:
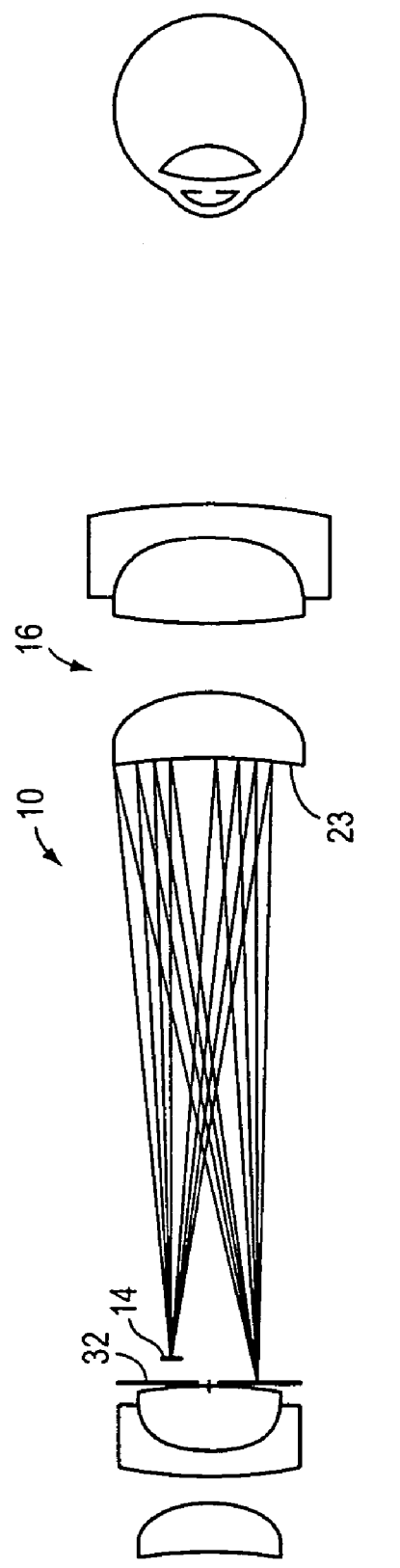
FIG. 1E is a functional diagram of an eye viewing device according to the invention showing incident light rays reflected from an objective lens.

Glare may be further reduced by shaping the first surface 23 of objective lens 16 so that first surface 23 is curved and substantially concentric with the center of aperture 33 as seen by the embodiment of FIG. 1E. This assures that light that is reflected from surface 23 is reflected to a point equal to and opposite light source 14 with respect to imaging axis 30. If light source 14 is positioned outside of the boundary dividing blocked and received light light defined by aperture 33, the concentric curved first surface 23 assures that internal glare resulting from light being reflected from surface 23 is blocked by aperture stop 32.

In addition to the above features reducing unwanted received light, glare can be reduced by disposing linear polarizers in the imaging and illumination paths in a crossed configuration.

A specific embodiment of an eye viewing device described generally with reference to FIGS. 1A-2A is described with reference to the physical layout diagram of FIG. 2B. This embodiment is advantageous compared to that in FIG. 2A because fewer lenses are used and because the non-eyepiece lenses are made from inexpensive molded plastic. The surfaces of the various elements of the illumination system of the eye viewing device of FIG. 2B are numbered surfaces 100 through 113. The elements containing these surfaces are briefly described hereinbelow.

Figures 2B, 2C:
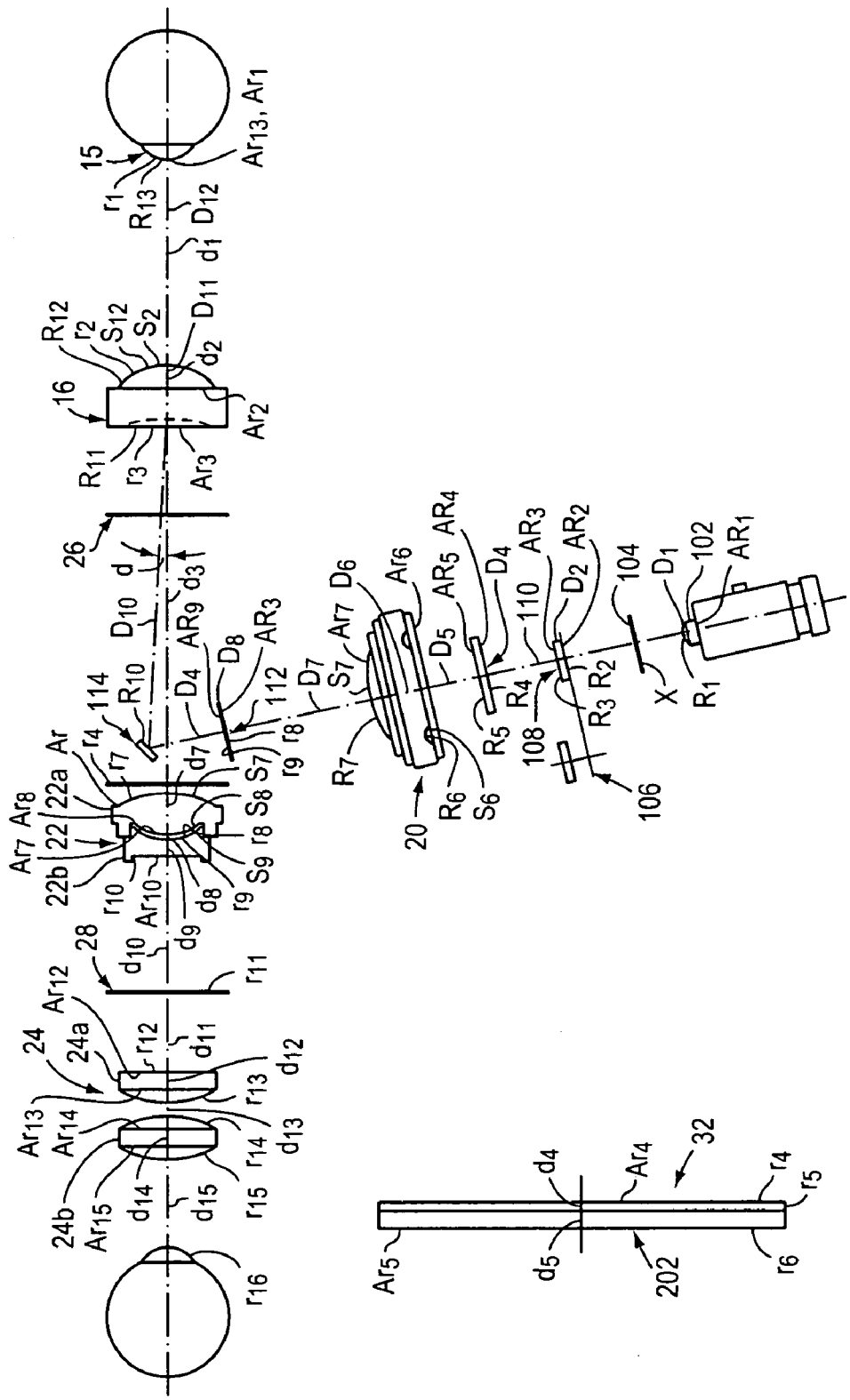
FIG. 2B is a schematic diagram illustrating a specific embodiment of the invention.
FIG. 2C is an exploded view of a section of the specific embodiment shown in FIG. 2A.

Referring to elements of the embodiment of FIG. 2B in greater detail, lamp filament 102 provides the source of illumination for the illumination system. In the embodiment of FIG. 2B, light source 102 preferably comprises a filament having a length of about 0.025 to 0.030 inches, a diameter of between about 0.0123 and 0.0136 inches, a number of turns of between 6.5 to 7.5, and a power rating of between approximately 3.25 and 3.33 watts. Lamp filament 102 is preferably oriented horizontally and rotated about 90 degrees from the viewing axis.

Device 10 may have an aperture window 104 that lies in plane X. In the case that device 10 includes an aperture window that lies in plane X, the aperture window should be formed at a position that is conjugate to a patient's retina. A smaller aperture provides easier view of a patient's retina through small pupils and cataracts. A larger aperture may be used for dilated pupils and for general examination of the central and peripheral retina.

Device 10 further includes an aperture wheel 106 comprising a plurality of optical elements which may be rotated into a position forward of filament 102 in the illumination optical path. Aperture wheel 106, for example, may carry an apertured glass 108. Apertured glass 108 may comprise plate glass having a lithography-formed slit or a machined slit in a metal substrate. The slit is helpful in determining various levels of retinal lesions, particularly tumors and edematous optic discs.

Apertured glass 108 may further comprise light filtering material. Preferably, apertured glass 108 filters red light and blue light. The red-free filter excludes red retinal rays for easy identification of veins, arteries, and nerve fibers. The blue filter is used in conjunction with fluorescein drops applied to the eye to detect corneal abrasions and other anterior and posterior segment lesions. Spacing apertured glass 108 a distance away from plane X minimizes the imaging of surface imperfections onto a retina. The illumination system shown in FIG. 2B further includes wide band hot mirror 110 that limits infrared and UV energy from entering a patient's eye.

Referring to further components of the illumination system of FIG. 2B, the illumination system includes condenser lens 20, which as described previously collects light from filament 102 and operates in combination with objective lens 16 to project an image of filament 102 onto or near a patient's cornea.

The illumination system shown in FIG. 2B further includes linear polarizer 112. As will be described further herein, linear polarizer 112 operates in combination with linear polarizer 202 of the imaging system to reduce corneal glare and glare that originates from the objective lens.

In the specific embodiment of the invention shown in FIG. 2B light source 14 is reflected by mirror 114. The magnification of filament 102 onto mirror 114 is about 1.5 in the embodiment shown. Mirror 114 is mounted at an angle, a, of 3.8 degrees from imaging axis 30 relative to objective lens 16. The orientation of the filament matches the geometric shape of the mirror, thus minimizing the mirror size.

Objective lens 16 operates in combination with condenser lens 20 to project an image of filament 102 onto a patient's cornea 15. Objective lens 16 and cornea 15 also form part of the imaging system.

Referring now to elements of the imaging system, retinal image light rays pass through cornea 15 in a collimated formation. Objective lens 16 focuses the parallel light from the patient's eye to a retinal image focal plane 26 between the objective lens and aperture stop 32, FIG. 2C.

Aperture stop 32 operates to block light that originates outside a 2 mm diameter circle located about 25 mm from the objective lens. This is the location of a patient's pupil when the instrument is in its nominal operating position.

Linear polarizer 202, as alluded to previously, operates in combination with linear polarizer 112 of the illumination system to reduce internal and external glare, especially internal glare from the objective lens and external glare attributable to corneal reflections. Linear polarizer 112 of the illumination system and linear polarizer 202 of the imaging system are disposed in a cross-polarized configuration.

Imaging lens 22 in the embodiment of FIG. 2B includes two lens elements, a first lens element 22A and second lens element 22B. The lens elements forming the imaging lens are separated by an air gap. Imaging lens 22 images the retinal image focal plane 26 of the objective lens 16 to the eyepiece focal plane 28.

A field stop (not shown) sized to correspond to the field of view may be disposed at eyepiece plane 28. Retinal image focal plane 26 and eyepiece focal plane 28 are conjugate to the patient's and viewer's retinas, respectively. Two internal image planes are required for proper orientation of the user's view of the patient's retina eyepiece lens 24 not labeled in FIG. 2b.

Eyepiece lens 24 comprises two lens elements 24A and 24B. The eyepiece assembly in the embodiment of FIG. 2B has an approximately +/−18 diopter focusing range. An apparatus for use in moving eyepiece lens elements 24A and 24B is described in commonly assigned copending U.S. patent application Ser. No. 09/774,726 entitled "Focusing Mechanism" filed Jan. 31, 2001 and incorporated herein by reference.

In developing guidelines for the manufacture of alternative embodiments of the eye viewing device having the general configuration shown in FIGS. 1A-2B, the inventors have found that it is advantageous to maintain certain dimensions of the system and relationships between certain components of the system within certain ranges. Specifically, with respect to the embodiment shown in FIGS. 2B and 2C, relationships described hereinbelow apply.

Referring to features of the illumination system, the inventors have found it advantageous to maintain the focal length of the condenser lens 20 between about 8 mm and 15 mm, and to maintain the magnification of the filament onto mirror between about 1 and 2. As has been explained with reference to FIG. 1E, internal glare is reduced by shaping the concave surface of objective lens 16 so that the concave surface is substantially centered about the center of aperture stop 32. The inventors have found the glare-reducing benefits of such a configuration are substantially yielded if the radius of the concave surface and the distance from the center of the aperture stop to the concave lens surface differ by approximately less than 10 percent. The length of imaging lens 22 should be maintained between about 10 mm and 20 mm. The inventors have also found that imaging lens 22 preferably operates in a reduction mode with a magnification of between about 0.5 and about 0.9.

The optical elements described with reference to FIG. 2B herein may be housed in a housing such as a housing shown in one of the commonly assigned Design patent application Ser. Nos. 29/137,181; 29/137,172; and 29/137,182 all entitled "Eye Viewing Device" and filed Feb. 14, 2001 and incorporated herein by reference.

An alternative embodiment of the invention is described with reference to FIGS. 3A-3C. In the embodiment shown in FIGS. 3A-3C, light source 14 is disposed directly in the field of view in a highly defocused position in relation to focal planes 26 and 28. By disposing light source 14 on imaging axis 30, light source 14 provides for maximally efficient illumination of a retina 19. Positioning the light source off-axis as is shown by light source 14' results in less-than-maximally efficient retinal illumination, but also reduces glare for reasons that have been discussed herein.

Light source 14 in the embodiment of FIGS. 3A-3C should be positioned in a highly defocused position in relation to any image plane of the eye viewing device conjugate to a patient's retina 19 in an operative position in relation to be positioned in a highly defocused position in relation to any image plane of the eye viewing device conjugate to a patient's retina 19 in an operative position in relation to device 10. As shown in the imaging system diagrams of FIGS. 3A-3C, a highly defocused position for source 14 in relation to an image focal plane conjugate to a retina is provided by disposing source 14 intermediate retinal focal plane 26 and imaging lens 22. In general, source 14 becomes less in focus at any plane conjugate to and including eyepiece focal plane 28 as the source is moved toward imaging lens 22 and away from retinal focal plane 26. Preferably, source 14 is positioned as close as is physically possible to lens 22. In some embodiments, the imaging device allows a field of view of at least 10 degrees to be illuminated, viewed and imaged.

Corneal glare can be reduced in the embodiment of FIGS. 3A-3C if source 14 is disposed in device 10 in a position that is conjugate to the surface of a cornea when the device is in an operative position in relation to a patient. If light source 14 is positioned conjugate to cornea 15, many light rays which do happen to be reflected from cornea 15 are imaged directly onto light source 14. If light source 14 is provided by a reflective element as shown, these light rays correspond to a cornea image and are blocked before reaching eyepiece focal plane 28, thereby reducing corneal glare.

In other specific examples of eye viewing devices designed according to the general configuration described with reference to FIGS. 1A-1E and 3A-3C, the objective lens 16 may be provided by a lens system having a focal length of about 25 mm, and a back focal length of about one-half the focal length. The eye viewing device may be configured so that the lens surface closest to the patient in the objective lens system is positioned about 25 mm from a patient's cornea when in an operative position. The objective lens system accepts parallel or nearly parallel light from a patient's eye and focuses the light to an internal image located at or near the back focal plane 26 of the objective. The objective lens system may have a diameter of about 25 mm. Imaging lens 22, meanwhile, may be provided by a lens system having a focal length of about 25 mm, a back focal length of about 18 mm and a clear aperture of about 20 mm. The imaging lens may project an internal image from the objective focal plane 26 to eyepiece focal plane 28 at a magnification of about 0.6.times. Eyepiece focal plane 28 may have an aperture of about 8 mm in diameter, corresponding to the focal plane diameter of a typical 20× eyepiece. The axial length from objective lens 16 to eyepiece focal plane 28 may be about 90 to 10 mm. In the illumination system described with reference to FIG. 3C, condenser lens 20 may be provided by a condenser system having a numerical aperture of about 0.2 to 0.4, working at a magnification of about 1× to 2×, with a focal length of about 9 mm. In the embodiment of FIGS. 1A-1E, aperture stop 32 may be positioned substantially normal to axis 30 and approximately halfway between the most rearward point of light source 14 and the most forward point of imaging lens 22. Aperture stop 32 may have an aperture diameter of about 4.6 mm.

Figure 4:
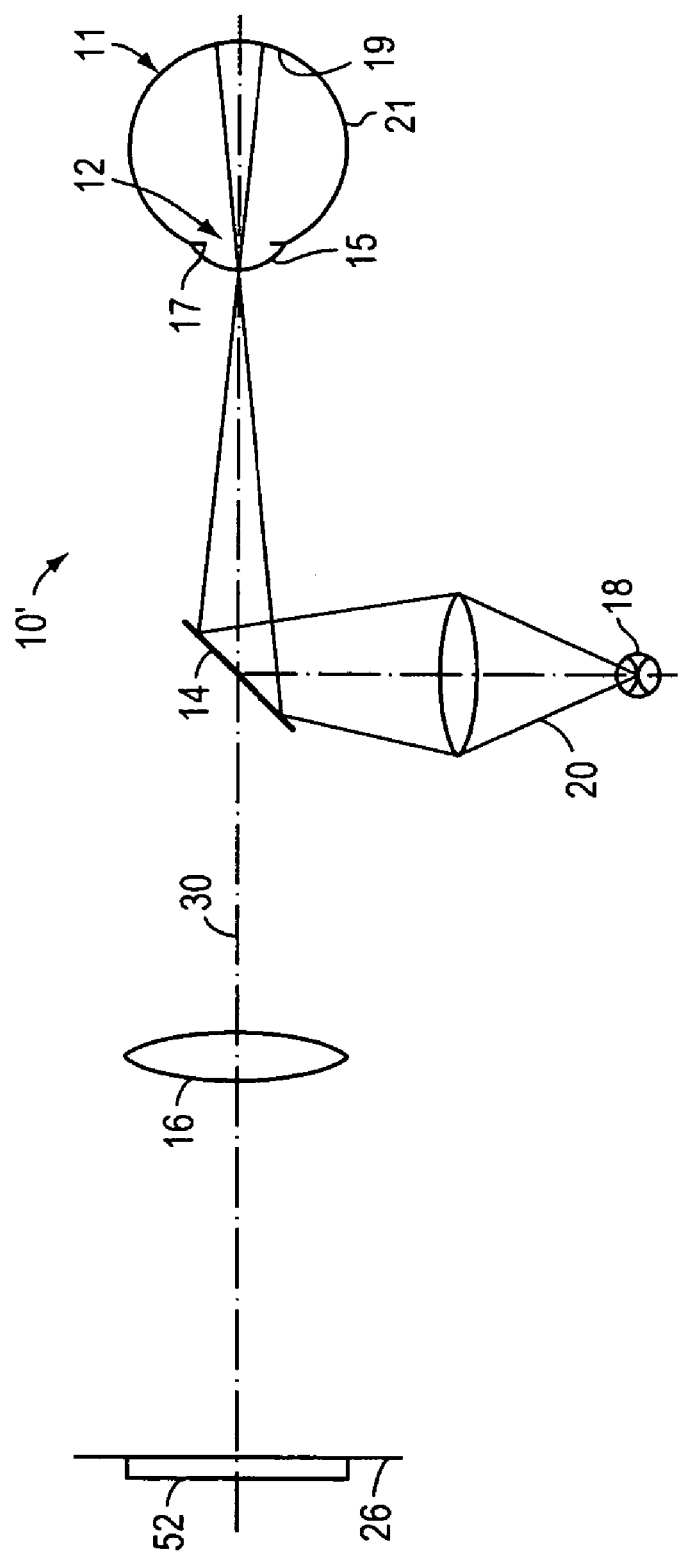
FIG. 4 is a functional schematic diagram of another embodiment of the invention having a defocused light source.

An alternative optical configuration for the eye viewing device of FIGS. 3A-3C having a defocused light source is described with reference to FIG. 4. In the eye viewing device of FIG. 4, light source 14 is disposed forward of objective lens 16 and imaging lens 22 is deleted. Light source 14 is disposed in a highly defocused position in relation to retinal focal plane 26 by disposing light source 14 in proximity with objective lens 16. In the embodiment of FIG. 4, objective lens 16 does not form part of the optical illumination system. Instead, illumination light rays which converge at a cornea 15 and diverge toward a retina 19 are formed by disposing condenser lens 20 in relationship with light source mirror 14 such that light rays reflected from the mirror converge after being reflected. Further with reference to the embodiment of FIG. 4, eyepiece lens 24 may optionally be removed and replaced with image sensor 52, such as a CCD image sensor, which is positioned on retinal focal plane 26. A processor system (not shown) in communication with sensor 52, can be configured to capture image signals generated by sensor 52, process such signals, and if desirable, electronically reverse or magnify any captured images to accomplish the function provided optically by imaging lens 22 of the eye viewing device of FIGS. 1A-3C.

The conventional lenses in the systems described hereinabove can be replaced with similarly functioning optical elements such as diffractive lenses, binary gratings, phase filters, holographic optical elements (HOE), gradient-index lenses, and hybrid optical elements.

Figure 5:
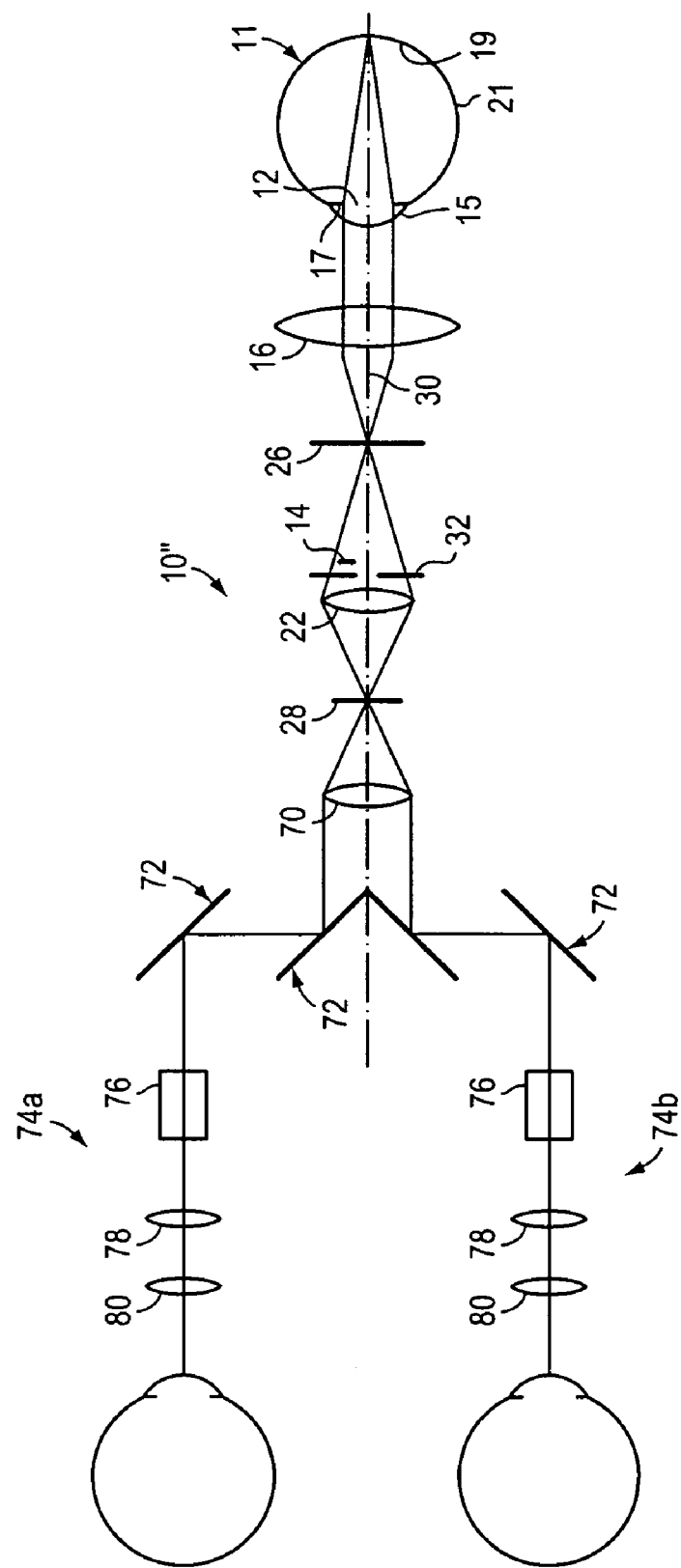
FIG. 5 is functional schematic diagram of the invention configured for binocular viewing.

It is believed that the invention can be adapted to provide binocular viewing as is illustrated by the embodiments of FIG. 5. As seen in FIG. 5, a binocular eye viewing device according to the invention typically includes a collimating optical element 70 for collimating light rays of the imaging path, and separating optics 72 for splitting light rays transmitted by collimating optics 70 into two separate imaging paths 74A and 74B. Separating optics 72 typically include a combination of such optical elements as prisms and/or mirrors. Continuing with reference to FIG. 5, binocular eye viewing device 10" may further include orientation optics 76 disposed in each binocular imaging path 74A, 74B for setting the orientation of images transmitted by separating optics as is necessary. Orientation optics 76 may include such optical elements as prism and/or mirror optical elements. Binocular eye viewing device 10" may further include decollimation optics 78 and eyepiece optics 80 disposed in each imaging path 74A and 74B. Each eyepiece optics 80 collimates light so that images can be perceived by a viewer. The eye tubes (not shown) of eyepiece optics 80 may be arranged in an orientation slightly diverging toward a viewer's eyes to approximate the direct viewing condition of a target by a pair of eyes.

Several functional aspects of the invention have been described. Certain additional features which may be incorporated in physical embodiments of the invention will now be described in detail.

Figure 6A:
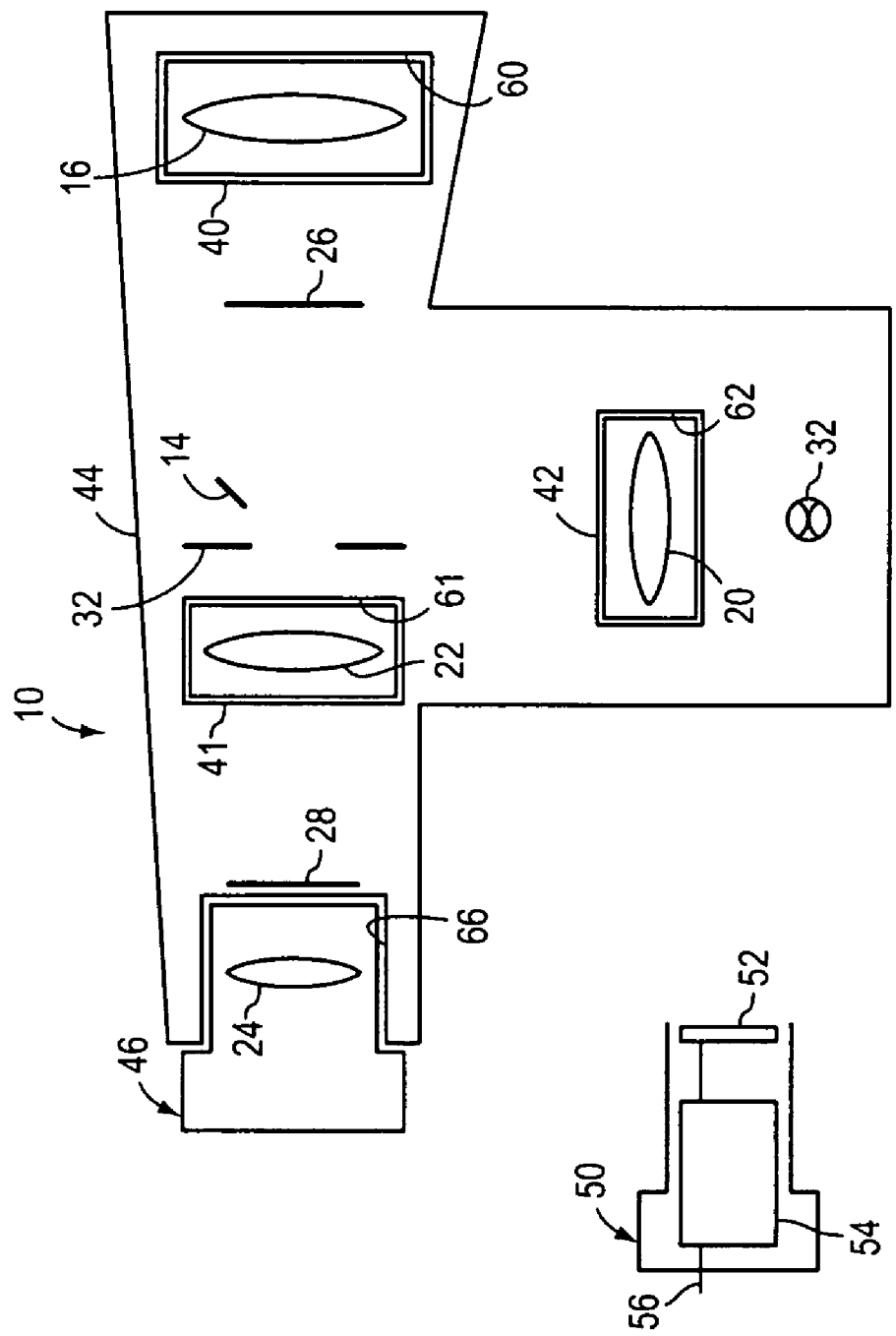

Shown in FIG. 6A is a physical schematic diagram of an embodiment of the invention which can be reconfigured for optimizing various functional aspects of the eye viewing device. In the embodiment of FIG. 6A, primary housing 44 of eye viewing device 10 includes lens holders 60, 61, 62 and 66 and replaceable lens modules 40, 41, 42 and 46 replaceably received in their respective holders. As will be explained hereinbelow, replacing a certain lens module or a grouping of lens modules changes functional aspects of the eye viewing device enabling the ophthalmoscope to be optimized for a specific intended use. For example, with reference to FIGS. 1A-1E, and 3A-3C, it is seen that the area of retina 19 that is illuminated by the illumination system depends on the diameter and optical power of objective lens 16 and on the magnification selected for the lens at the operative position of the eye viewing device. This area corresponds to the angle a as shown in FIGS. 1A and 3C. The field of view of the imaging system, meanwhile, also depends on the diameter and optical power of objective lens 16 and on the magnification of the lens at the operative position of the eye viewing device.

It is desirable that eye viewing device 10 images a wide field of view. While a wide field of view and illumination angle, a, are highly desirable for an accurate and efficient diagnosis of various problems, a smaller field of view and illumination angle are desirable for ease of use. As the angle of illumination, a, becomes less steep, illumination light rays are more easily directed into an eye through a pupil, so that entry into an eye is easier. This is because as the illumination angle, a, becomes less steep, light rays from source 14 can be directed through pupil 12 over a greater range of cornea-to-lens distances. Accordingly, in view of the above, it would be beneficial to provide an eye viewing device which could be configured either for optimized field of view or optimized ease of use.

In a preferred embodiment, the imaging system of device 10 images a field that contains the area of a retina that is illuminated by the illumination system. Most preferably the area of the retina that is imaged by the imaging system is about 15 percent to 30 percent larger than the area that is illuminated. This feature provides improved orientation of a viewed field and reduces alignment considerations between illumination and viewing.

A possible embodiment of reconfigurable eye viewing device according to the invention is described with reference to the physical schematic diagram of FIG. 6A. This particular physical layout diagram includes first and second lens modules 40 and 41. First lens module 40 includes objective lens 16, while second lens module 41 includes imaging lens 22. While the field of view and illumination angle depend mainly on the sizing, optical power, and magnification selected for objective lens 16, imaging lens 22 will normally be replaced along with lens 16, since the sizing and optical power of lens 16 are coordinated with those of lens 22. The housing 44 and lens modules 40, 41 are complementarily designed so that the modular lens modules can be manually removed and replaced from housing 44 while maintaining a common eyepiece focal plane 28. In a reconfigurable eye viewing device, a first set of lens modules can be provided to configure the eye viewing device for imaging a wide field of view, while a second set of modules can provide a reduced field of view (but with increased magnification), making the instrument easier to maneuver into an operative position. Such a device can be made easier to use simply by replacing the first set of lens modules with the second set of lens modules.

To complement the change in field of view accomplished by changing the first and second lens modules, the illumination condenser system may also be changed in a modular fashion to optimize the illumination characteristics to suit the user's needs. In all condenser systems with a given condenser size, the ability to collect the light from a light generating light source is balanced with the angle at which the light can be transmitted and the magnification at which the image of the light generating light source is projected. The lenses inside the illumination lens module 42 can be selected such that the illumination system matches the illumination numerical aperture of the given objective module 40.

In a further alternate embodiment, the invention can be adapted to capture electronic images representing an imaged retina. One such embodiment is described with reference to FIG. 6A. In FIG. 6A, an eye viewing device 10 is shown that can be reconfigured for electronic image capture. FIG. 6A shows an eye viewing device adapted so that eyepiece module 46 can be replaced with a video (or electronic imager) module 50. It is seen that eye viewing device 10 normally includes an eyepiece module 46 having an eyepiece lens 24 which collimates imaging light rays so that a retinal image can be viewed by a user. Eyepiece 46 can be replaced with video module 50 which includes certain components that configure the eye viewing device for video capture. In particular, a video module 50 may contain an image sensor 52, such as a CCD or CMOS image sensor, which is in an operative position in relation to the imaging system when the video module is installed in holder 66. The image sensor 52 is in electrical communication with a processor system 54, typically including a microprocessor and associated memory, which may be programmed to control image sensor 52 and to capture and, possibly, to store image data generated by and received from image sensor 52. While processor system 54 is shown as being disposed in video module 50, it is understood that processor system 54 could be disposed external to video module 50. The video module 50 may further be in communication with display screen external to housing 44 and module 50 and/or a processing system external to housing 44 and to module 50 via a combination of communication link components which comprises cable 56 and associated input/output interfaces, for example, so that video image information corresponding to image signals generated by image sensor 52 can be displayed or otherwise output, and possibly archived. The communication link including cable 56 can be replaced with a combination of communication link components which comprises a wireless transmitter-receiver combination. Image information corresponding to image signals generated by image sensor 52 can also be communicated to electronic components external to module 50 and housing 44 with use of a combination of communication link components including transportable memory structure such as a computer disk, a compact disk or a memory stick. An encoder for encoding such a memory structure may be located in a module as described herein or external to a module in housing 44.

Video module 50 can be designed so that image sensor 52 lies on eyepiece focal plane 28 when module 50 is in an operative position in holder 66. It is seen that an eye viewing device of the invention can be configured for video capture by replacing eyepiece module 46 with a video module 50 without adding or replacing additional lenses of the imaging system. Alternative sized image sensors may also be used, with the addition of image resizing lenses. Such a configuration shifts the location of focal plane 28.

Figure 6B:
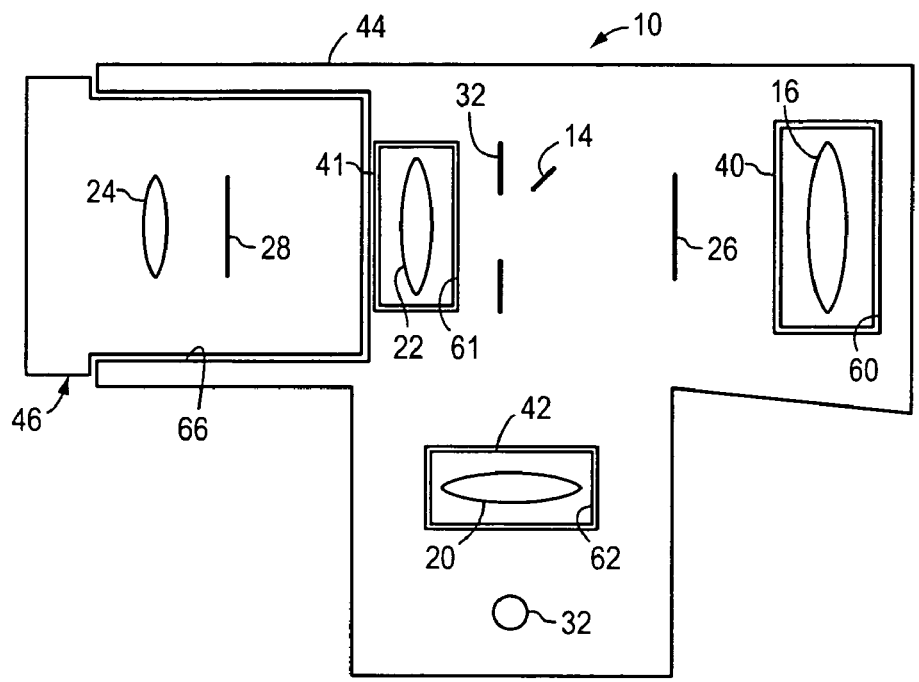
Figure 6C:
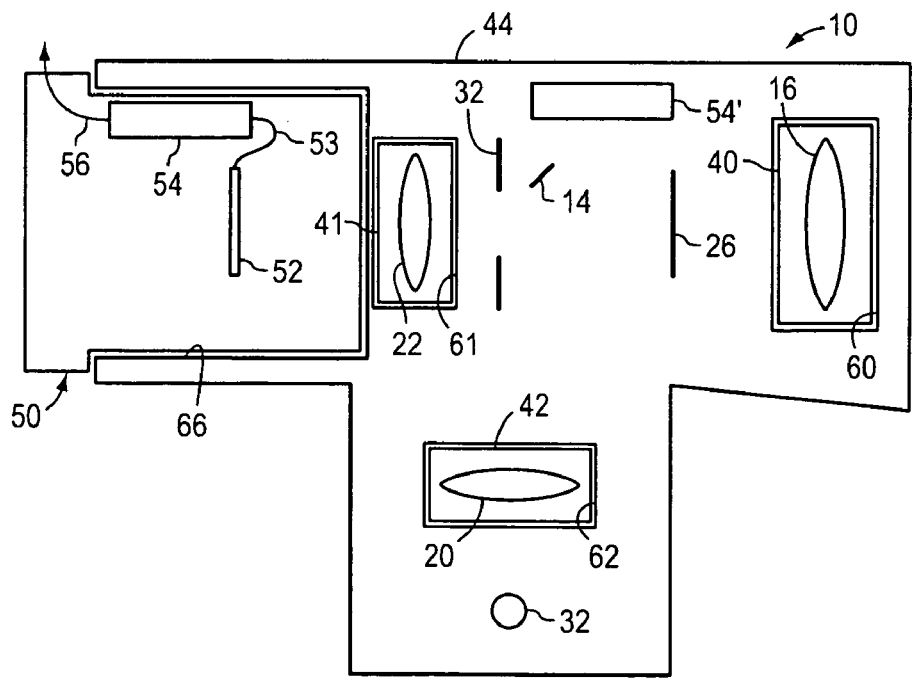

Eye viewing devices having a viewing module holder for receiving various alternative types of viewing modules are shown in FIGS. 6B-6I. Viewing module 46 of FIG. 6B is an alternative version of eyepiece viewing module 46 shown in FIG. 6A. Viewing module 50 of FIG. 6C is an alternative version of video viewing module 50 shown in FIG. 6A.

Figure 6D:
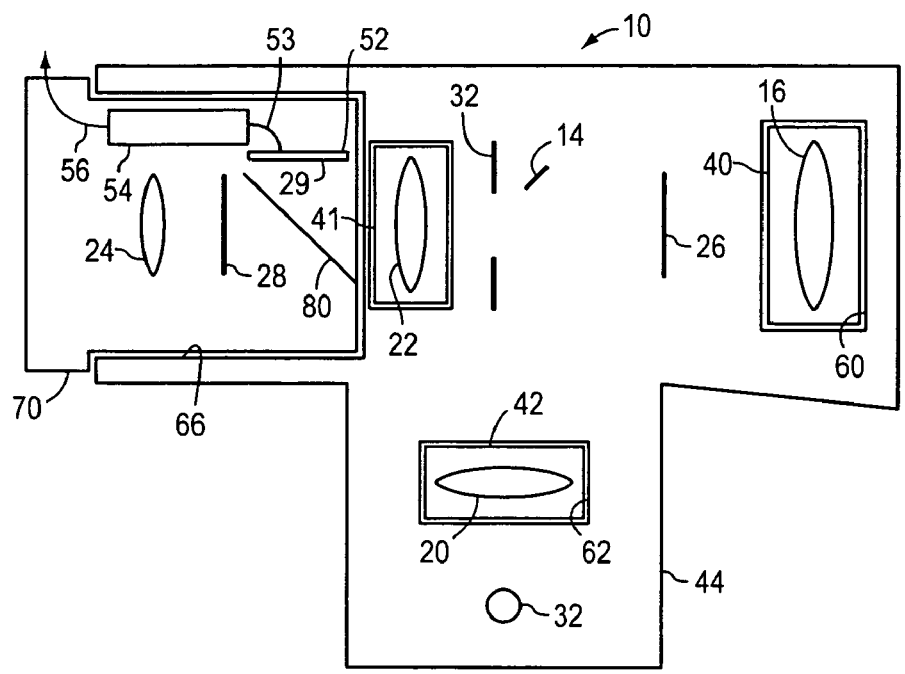

FIG. 6D shows a viewing module 70 adapted to provide both optical viewing and video capture. Viewing module 70 includes a beam splitter 80 for splitting the retinal image and generating a pair of retinal image focal planes, a first, eyepiece focal plane 28, and a second retinal image focal plane 29 at which image sensor 52 is disposed. Viewing module 70, like viewing module 50, includes processor system 54 in communication with image sensor 52 via lead 53 for controlling image sensor 52 and capturing and possibly storing image data corresponding to image signals generated by image sensor 52. Processor system 54 may be programmed to electronically generate a mirror image of the image formed at image sensor 52. Video module 70 further includes lead 56 for providing communication of video images and data with external displays and/or external processing systems.

Shown as being located inside module 70, processor system 54 could in the alternative be positioned at a position external to the module but inside housing 44 as is indicated by processor system 54' of FIG. 6C or at a location external to both module 70 and housing 44. If the processor system associated with any one of the viewing modules described herein having an image sensor 52 is located external to the module but inside housing as is indicated by the embodiment of FIG. 6C, then the processor system 54' and image sensor 52 should be arranged so that an electrical connection is made between the processor system 54' and image sensor 52 when the viewing module having the image sensor is fitted into the viewing module holder 66 of the eye viewing device 10. Such an electrical connection can be provided by positioning complementarily mounted mating connectors in the viewing module and primary device housing 44, respectively, such as mating connectors 85 shown in FIG. 6I.

Mating connectors such as connectors 85 may also serve to facilitate linkage between an electrical component of any one of the viewing modules described and a power supply of a device. For example, mating connectors 85 in the embodiment of FIG. 6I may be adapted so that processor system 54 is electrically linked to a battery supply power source in proximity with light source 32 when connectors of mating connectors 85 are mated together.

Further, it will be understood that the processor system receiving image signals from image sensor 52 in any one of the embodiments described herein need not be located within a viewing module or within housing 44. The processor system receiving image signals from image sensor may be located externally relative to both housing 44, and the viewing module and may be provided, for example, by a processor system of a personal computer. If an eye viewing device according to the invention includes an image information processing processor system located a substantial distance away from an image signals generating image sensor, it is useful to configure the processor system and image sensor so that the image sensor and processor system communicate with one another via a high speed communication technology, such as Universal Serial Bus communication technology or Firewire technology.

Figure 6E:
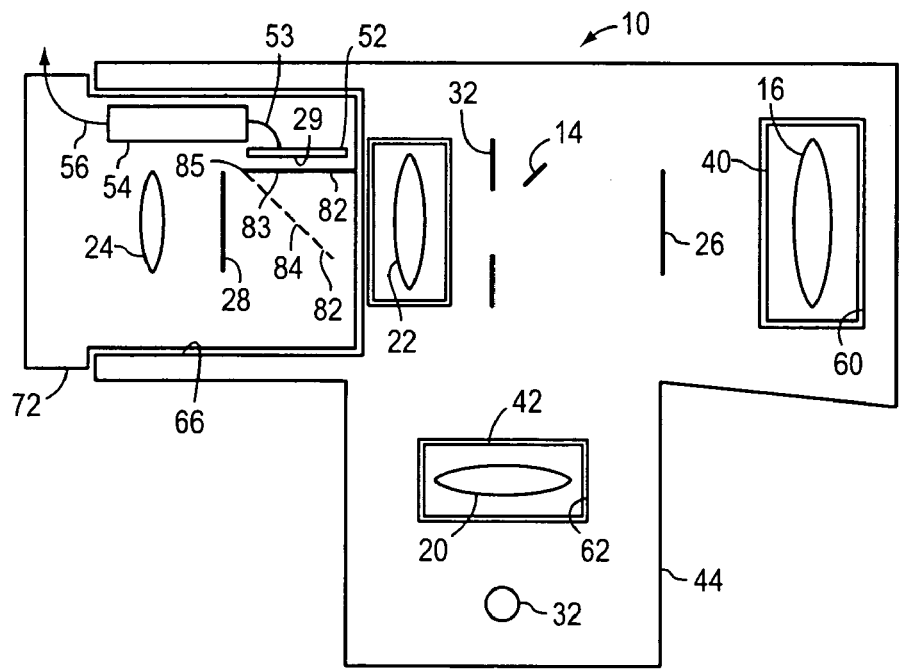

An embodiment of a viewing module similar to the viewing module 70 of FIG. 6D is shown in FIG. 6E. The viewing module of FIG. 6E includes all of the elements of viewing module 70 of FIG. 6D except that viewing module 72 includes a two-position mirror 82 in place of beam splitter 80 FIG. 6D. Two-position mirror 82 is moveable between two positions 83, 84. In a first position, indicated by solid line 83 mirror is in a position such that a retinal image is formed at eyepiece focal plane 28. In a second position, indicated by dashed line 84, mirror 82 is in a position such that a retinal image is formed at image sensor 52. Mirror 82 may be mounted using a hinge within viewing module 72 as is indicated by pivot point 85. Mirror 82 may be adapted to be manually moveable between the first and second positions or else mirror 82 may be adapted to be movable by means of motor motion. Mirror 82 can be understood to operate in the same manner that the mirror in a single lens reflex (SLR) camera operates, alternatively passing light to a viewfinder in one position, and in the second position, passing light to a recording medium such as photographic film, or to an electronic imaging device. Again, similar to a single lens reflex camera, in which a mechanical or electronic shutter is provided in order to control an exposure (or integration) time, devices according to the invention can comprise a shutter for the purposes of controlling duration of illumination. With an electronic imaging device, one can additionally control the integration time. The integration time of the electronic imager (or second time interval) is adjusted to be different than that of the viewing time duration (or first time interval). In an alternative embodiment, mirror 82 rests in position 84, and is electronically controllable to become more reflective, thereby passing light to image sensor 52, or to become less reflective (more transparent) thereby passing light to the eyepiece.

As should be clear from the above description, some systems, such as beamsplitter systems, provide a first fraction of illumination to one receiver (such as the eyepiece) and another fraction of the illumination to a second receiver (such as an imager) at substantially contemporaneous and overlapping periods of time. It should be equally clear that other systems, such as systems similar to SLR camera systems, provide a first fraction of illumination to one receiver (such as the eyepiece) and another fraction of the illumination to a second receiver (such as an imager) at substantially non-overlapping, sequential or serial, periods of time.

Figure 6F:
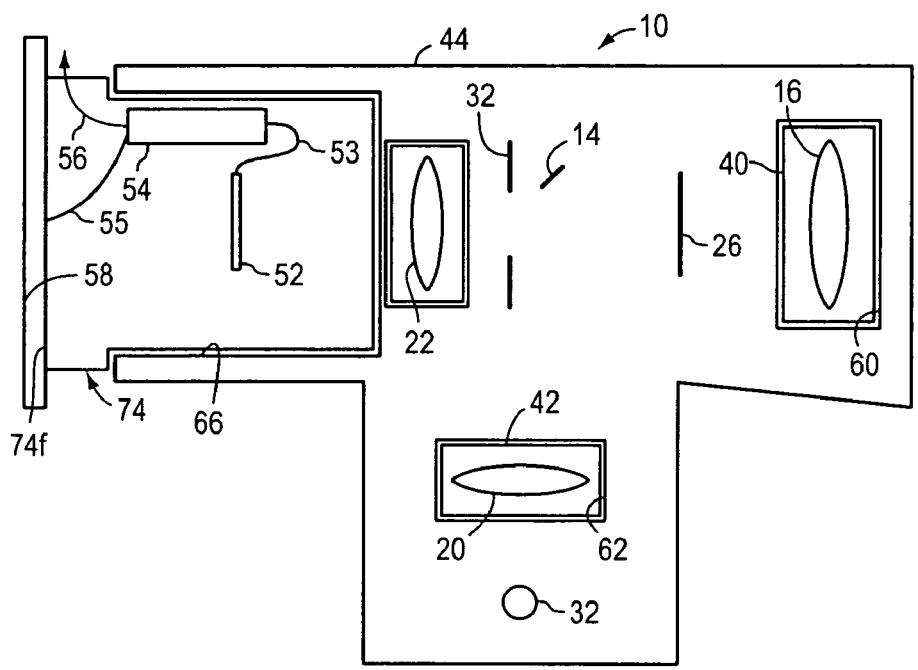

In FIG. 6F, a viewing module received in a viewing module holder 66 is shown that contains a built-in display 58. In viewing module 74, image sensor 52 is positioned at the position of eyepiece focal plane 28 when the module is properly received in holder 66. Image sensor 52 is in communication with processor system 54 programmed to control and capture image data corresponding to image signals generated by image sensor 52. In addition to being in communication with image sensor 52, processor system 54 is in communication via lead 55 with a display 58 which is built directly into module 74. Display 58 may be provided, for example, by a light weight LCD display as is well known. Display 58 is conveniently located at the face portion 74f of viewing module 74 as is indicated by FIG. 6F. Viewing module 74 may include, in addition, a lead 56 for providing external communication of video images and/or other data with an external display or processing system located externally with respect to the viewing module and housing 44.

Figure 6G:
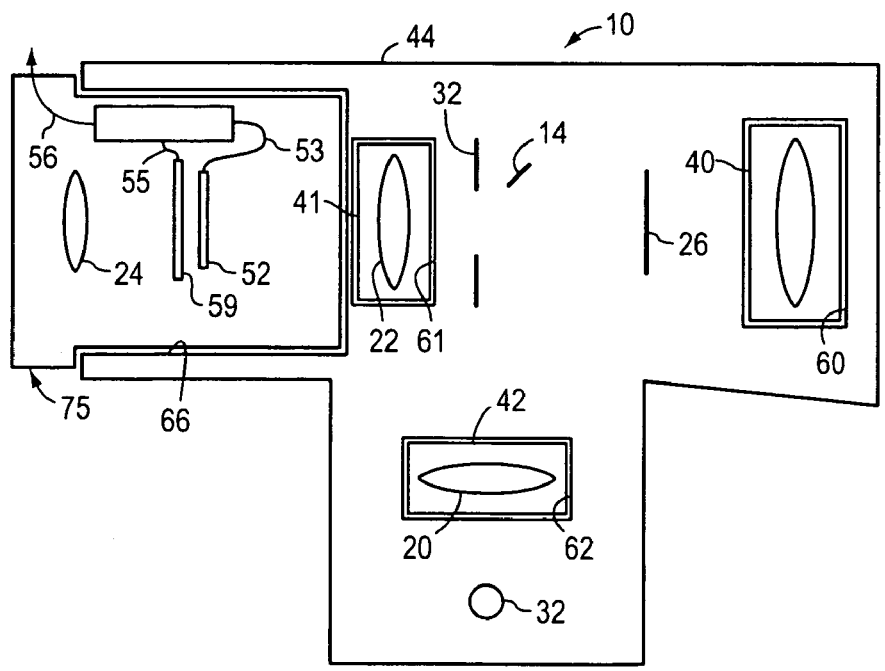

The viewing module 75 of FIG. 6G is similar to the viewing module of FIG. 6F except that externally mounted display 58 is replaced with an interior mounted display 59 mounted at an interior of module 75. Display 59 is preferably a miniature LCD display. Viewing module 75 may include an eyepiece lens 24 for collimating light rays generated by display 59.

Figure 6H:
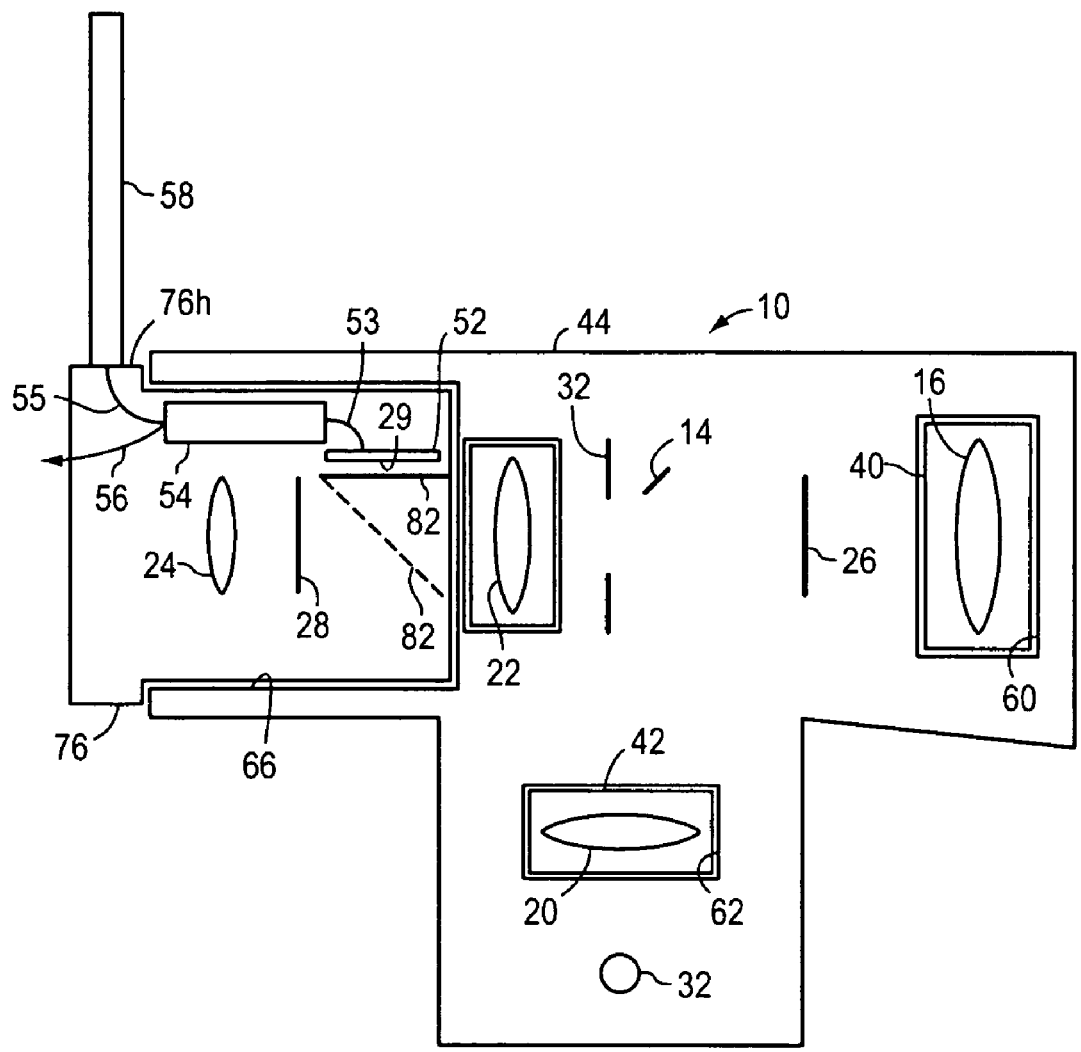
Figure 61:
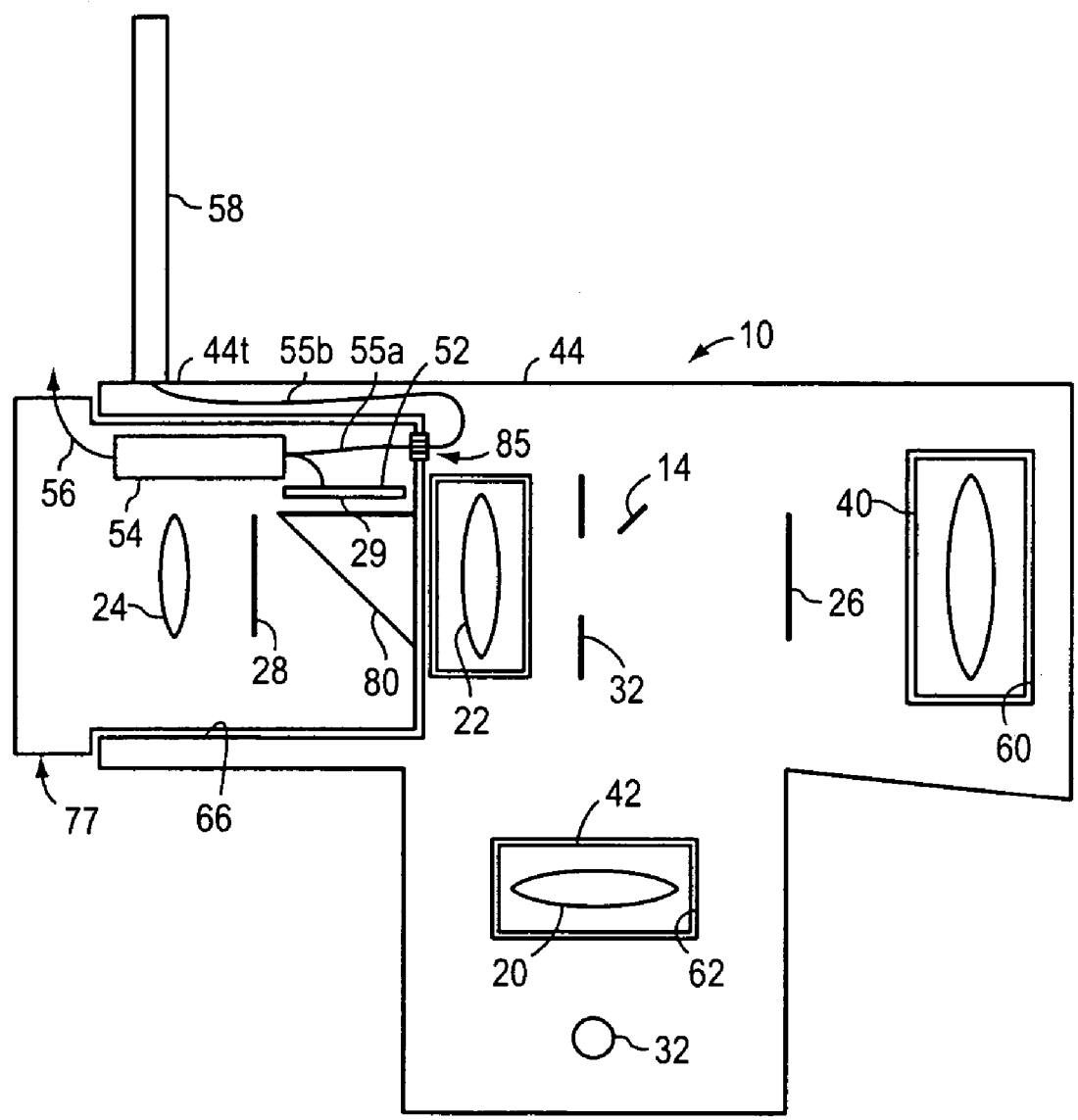

Alternative embodiments of eye viewing devices having built-in or attachable displays are shown in FIGS. 6H and 6I. In the embodiment of FIG. 6H, viewing module 76 includes a display 58 mounted to a top surface 76t of an externally extending portion of module 76. In the embodiment of FIG. 6I, a display 58 is fixedly mounted to a top surface 44t of primary device housing 44. Display 58 could in the alternative be detachably mounted to housing 44 or pivotally attached to housing 44. In the embodiment of FIG. 6I, viewing module 77 includes lead 55A that matingly connects to lead 55B in communication with display 58 when module 77 is received in holder 66. The mating connection between leads 55A and 55B may be provided by complementarily mounted mating connectors 85.

The viewing modules 46, 50, 70, 72, 74, 75, 76 and 77 preferably have similarly sized outer housings so that each may be fitted into a single viewing module holder which is adapted to receive one viewing module at a time. One or more of the above viewing modules may be sold or made available in a system wherein viewing modules can be interchanged for optimization of an eye viewing device for a particular application. A viewing module according to the invention is adapted to be held in place in a complementarily formed holder by friction forces or other known retaining means.

Of course, the elements incorporated in the above-described removably installable viewing modules 46, 50, 70, 72, 74, 75, 76 and 77 can be permanently mounted in an eye viewing device that does not contain a viewing module holder.

Figure 6J:
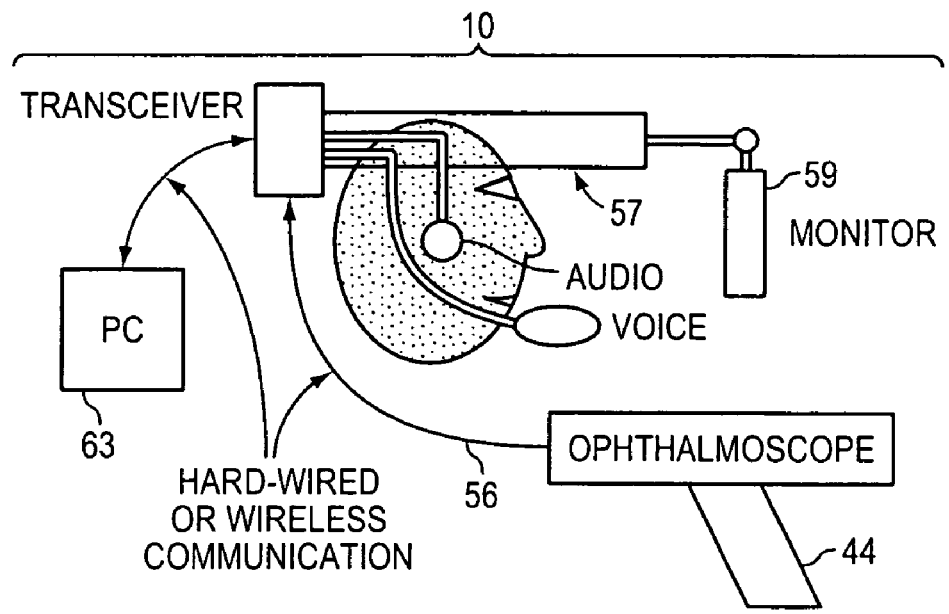
Figure 6K:
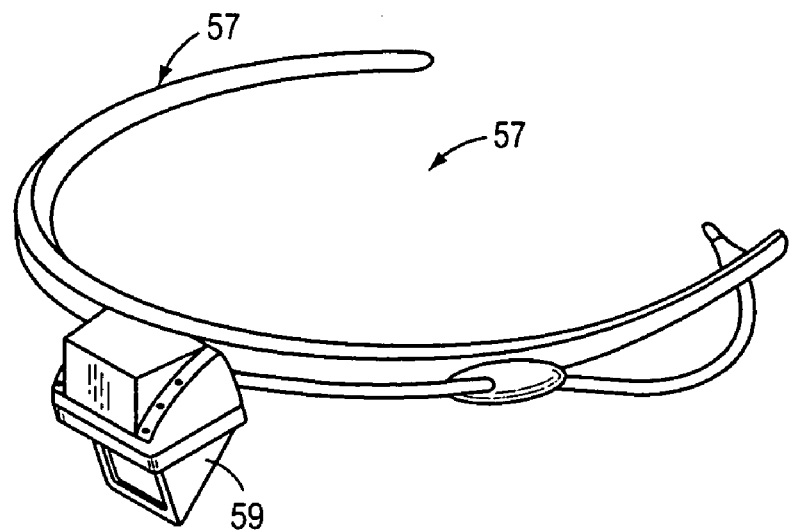

As indicated above, viewing modules having a processor system 54 for processing images may include a lead 56 for providing communication between the processor system and an external display device or processor system external to module and housing 44. One type of external display which may be in electrical communication with viewing module having a video processor system is a head mounted display assembly 57 including a display 59 as shown in FIGS. 6J and 6K. Head mounted displays are useful in enhancing the mobility of a viewer. In the embodiment of FIG. 6J, an eye viewing device 10 includes a head mounted display assembly 57, voice activated control, an audio feedback means, and a personal computer 63. From the embodiment of FIG. 6J it is seen that the elements of an eye viewing device can be spread out over several physically separate components including primary device housing 44, a viewing module, a personal computer 63 and a video assembly 57.

It will be understood that the image sensor referred to in any one of the above viewing modules having an image sensor may be any commercially available image sensor. For example the image sensor may be a visible light image sensor or an image sensor that is selectively responsive to light in a specific band, such as an infrared or ultraviolet image sensor. The image sensor may also be a spectral imaging type image sensor which makes available spectral profile data characterizing the spectrum of light incident at each pixel of the image sensor. In addition, processor system 54 and image sensor 52 can be incorporated in a single piece of silicon. For example, image sensor 52 and processor system 54 can readily be integrated in a single piece of silicon utilizing CMOS fabrication methods.

Further, it will be understood that any one of the electrically conductive lines described herein, e.g. lines 53, 55, 55a, 55b and 56 could be replaced with a wireless data communication link such as an IR link or an RF link, for example an RF link utilizing the "Blue Tooth" communication protocol.

Figure 7A:
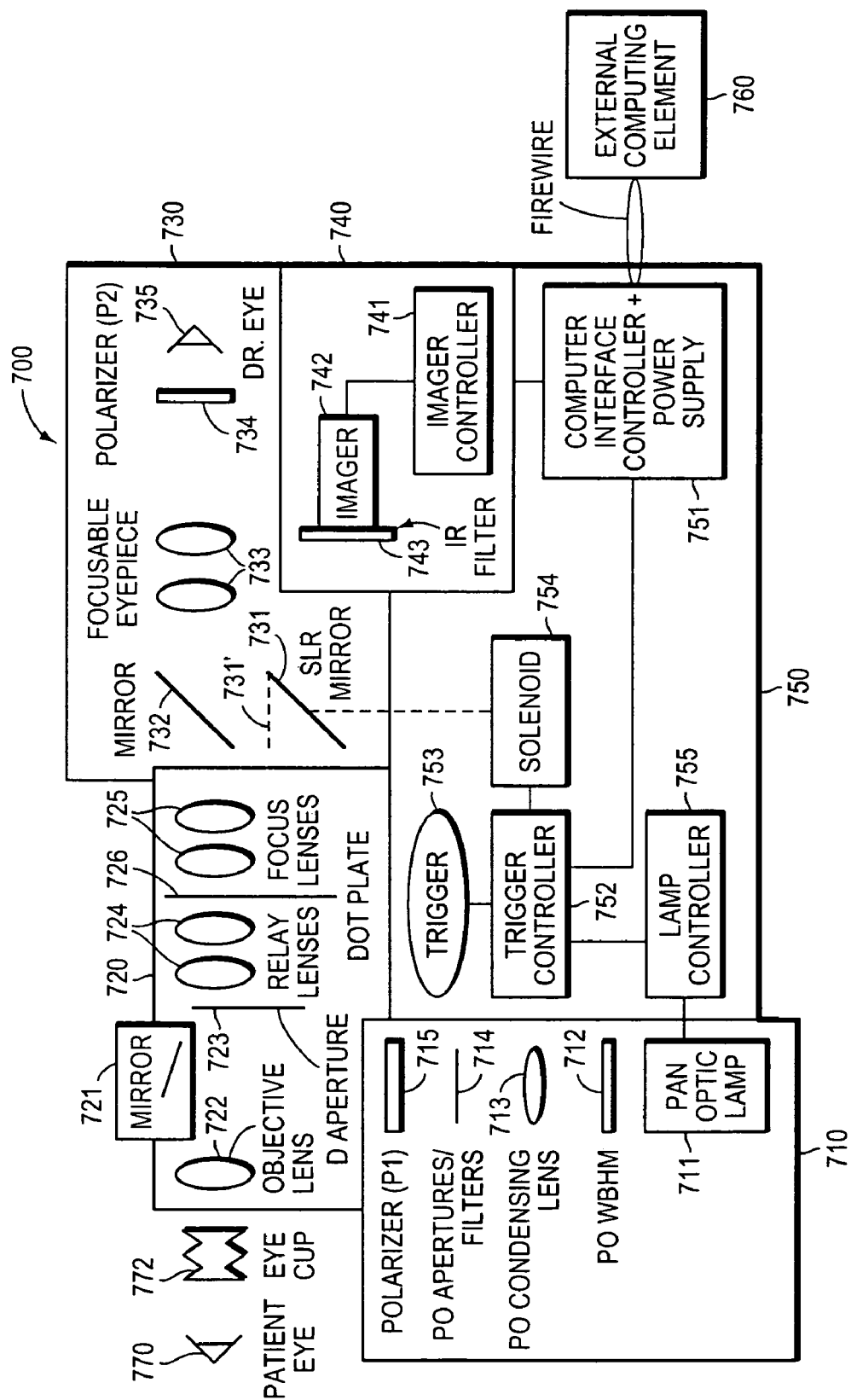
FIG. 7A is a schematic diagram of another embodiment of the digital documenting ophthalmoscope according to principles of the invention.
Figure 7B:
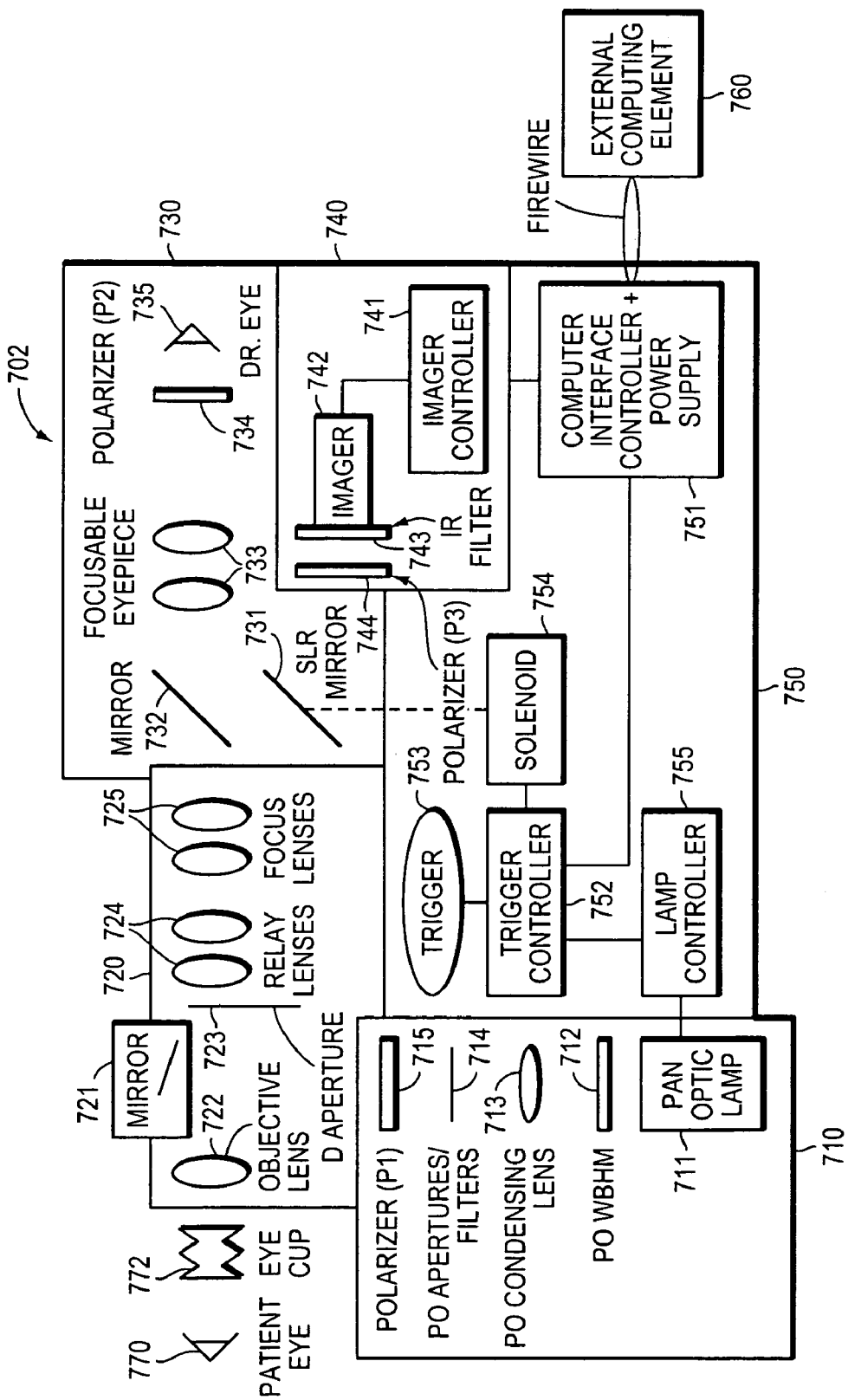
FIG. 7B is a schematic diagram of a further embodiment of the digital documenting ophthalmoscope according to principles of the invention.

FIGS. 7A and 7B are schematic diagrams of other embodiments of the digital documenting ophthalmoscope according to principles of the invention. The digital documenting ophthalmoscope, also referred to as a digital fundus imager, provides some important advantages as compared to conventional ophthalmoscopes. The invention also provides a method of assessing a condition of an eye in a single interrogation of the eye, comprising viewing the eye in a true color live view by an operator, and capturing an image of the eye in an imager.

Ophthalmoscopes are among the most commonly used medical devices. They are used for a variety of examination and diagnostic procedures in the eye. In the field of optometry, fundus (or retinal) cameras are used to document the condition of the retina as viewed with an ophthalmoscope (or other diagnostic instrument). When two separate instruments are used (one to diagnose, one to document, often by two different individuals), it is readily recognized that the images that are captured will not always completely reflect the conditions that the practitioner wishes to document. Combining these two instruments requires finding an optimal tradeoff between image quality, image field of view and small pupil performance, since these parameters are all related to the amount of light in the system. Traditional fundus cameras solve this tradeoff by using IR/flash illumination. Flash illumination is unacceptable for use as a live-view diagnosing instrument because the practitioner cannot examine the fundus in a meaningful manner during the short duration of the flash. "Live" viewing generally is best performed using substantially continuous illumination, or illumination lasting at least for a duration sufficient for easy observation by a human operator (e.g., some seconds or longer, rather than milliseconds). Another option would be to use an extended series of pulses of illumination that appear to be substantially continuous to a human observer. IR illumination is unacceptable for use as a live-view diagnosing instrument because the practitioner cannot examine the fundus using IR illumination, which is not detected by the human eye. The digital documenting ophthalmoscope provides both a live, diagnosable view by a practitioner and a captured documenting image in a single instrument in real time. In addition to this unique two-in one functionality, some additional benefits that the digital documenting ophthalmoscope provides include: true non-mydriatic optics that enable a field of view of up to 25 degrees through a pupil as small as 2 millimeters without use of a flash; the ability to capture, store, and print images; the ability to use the images for such activities as patient education, ophthalmic practice management including record-keeping and documentation for purposes of reimbursement, and use of images for "diagnosis at a distance," (or telemedicine) for example by communicating one or more captured images over a communication medium such as a telephonic connection or over a network such as the Internet, a LAN, or a WAN, for viewing by a practitioner for consultation or diagnosis in substantially real time, even when the patient and the practitioner are in physically remote locations one from the other; and use of stored images for archival purposes, such as following the condition of an eye of a patient over time. The captured images can include or have associated therewith a time and/or date stamp, an identifier for the patient, an identifier as to whether the image is one of the right or left eye (e.g., an "R" or an "L" can be added to the image electronically, for example in a corner thereof), an identifier of the practitioner, and such information as notes or other information of significance. The digital documenting ophthalmoscope can be optionally mounted on a cart, for use as a mobile device in an office or hospital setting, or it optionally can be a small, easily portable, handheld unit suitable for use in the office or in the field, for example in an ambulance. Yet another benefit is the possibility of providing the digital documenting ophthalmoscope at a competitive price, especially as compared to the price of two distinct instruments.

Turning now to FIG. 7A, a first schematic diagram depicts one embodiment of the digital documenting ophthalmoscope 700, which comprises a number of modules. An illumination module 710 is provided as a component of the digital documenting ophthalmoscope 700. The illumination module 710 provides illumination for both the true color live view of the eye of the patient by the operator of the instrument, as well as the illumination for the digital imaging operation of the instrument. The illumination module 710 comprises a panoptic lamp 711, a panoptic Wide Band Hot Mirror (WBHM) 712, one or more panoptic condensing lenses 713, one or more panoptic aperture plates or filters 714, and a polarizer 715 that linearly polarizes the illumination beam before it exits the illumination module 710. The illumination module 710 provides light having controlled intensity and spectral characteristics. The panoptic lamp 711 is controlled by a lamp controller 755, which is in electrical communication with the lamp 711.

The digital documenting ophthalmoscope 700 further comprises an optical module 720 that handles the transmission of illumination from the illumination module 710 to an eye 770 of a patient and handles the collection of reflected light from the eye 770 for provision of the reflected light to a viewing module 730 for ultimate delivery to an eye 735 of a human operator for a "true color live view" and to an imager module 740 for delivery to an imager 742 for capture of a digital image. The digital image can be a color image, a black and white image, or a grayscale or false color image, as may be useful.

The optical module 720 comprises a mirror 721 or equivalent structure to steer and project the illumination beam from the illumination module 710 toward the eye 770 of the patient. The illumination passes through one or more objective lenses 722 as it propagates toward the eye 770 of the patient. The one or more objective lenses 722 focus and direct the illumination. Optionally, an eye cup 772 is provided between the eye 770 of the patient and an extremity of the instrument 700. Light that is reflected from the eye 770 of the patient is collected by the one or more objective lenses 772, through an appropriate shape aperture stop 723, and through one or more relay lenses 724. The reflected illumination beam passes through a transparent portion of a dot plate 726, and the internal glare reflections from one or more surfaces of the objective lens are intercepted by an opaque portion of the dot plate 726, as is described in more detail below. The portion of the reflected illumination than passes through the transparent portion of the dot plate 726 passes through one or more focus lenses 725 before exiting the optical module 720.

The reflected illumination exiting the optical module 720 is directed into either or both of the viewing module 730 and the imager module 740. In one embodiment, a mirror 731, similar to the mirror in a single lens reflex (SLR) camera, is provided. The SLR mirror 731 is movable between a first position (shown in FIG. 7A as a solid line) and a second position (shown in FIG. 7A as a dotted line 731'). In the first position, mirror 731 causes illumination exiting from the eye 770 to reflect toward mirror 732, and to reflect therefrom toward focusable eyepiece 733, which comprises one or more lenses, and to pass through polarizer 734, and then to the eye 735 of an operator, such as a doctor, to provide a "true color live view" of the eye 770 of a patient, or of a portion thereof, such as the fundus of eye 770. In some embodiments, alternatives to the mirror 731 are employed, which alternatives permit simultaneous illumination to both the eye 735 of the operator and to the imager module 740, as are described in greater detail below.

When mirror 731 is situated in position 731', the illumination that exits from the eye 770 is not intercepted by mirror 731, but passes into the imager module 740. The imager module 740 comprises an IR filter 743, an imager 742 such as a CCD imager having a two-dimensional array of photosensitive elements or pixels, and an image controller 741 in electrical communication with the imager 742. The IR filter 743 passes illumination having wavelengths in one or more pass bands, and absorbs illumination having wavelengths in at least one absorption band, the wavelengths of the pass band and the wavelengths of the absorption band being mutually exclusive. The illumination that reaches the imager 742 is converted to electrical signals on a pixel by pixel basis, as is understood in the light sensing arts, and the electrical signals are extracted from the imager 742 under the control of the imager controller 741, using conventional control procedures for extracting signals from two-dimensional imaging chips.

The digital documenting ophthalmoscope 700 further comprises a control module 750 that controls and synchronizes the operation of the various modules and components of the digital documenting ophthalmoscope 700. Control module 750 comprises a computer interface controller and power supply 751 that is a microprocessor-based programmable controller, and a power supply such as a battery (in a portable unit) or a conventional power supply fed from a wall plug. In some embodiments, a machine-readable memory is provided with the computer interface controller and power supply 751 for purposes of holding data extracted from the imager 742, and/or for holding one or more commands for operating the computer interface controller and power supply 751. The computer control interface and power supply 751 is in electrical communication with the imager controller 741, both for controlling the imager controller 741 and for receiving from the imager controller 741 data corresponding to an image of the eye 770 of the patient. Computer interface controller and power supply 751 is also in electrical communication with a trigger controller 752, and in communication by wireless connection (or alternatively by a wire connection) with an external computing element 760, such as a conventional commercially available laptop or desktop computer. The trigger controller 752 and the computer interface controller and power supply 751 communicate to exchange commands and timing signals, such as a trigger signal indicating activation of trigger 753 in electrical communication with trigger controller 752, or signals from computer interface controller and power supply 751 to trigger controller 752 relating to illumination levels to be achieved by panoptic lamp 711, or timing signals for moving SLR mirror 731 to position 731' to accommodate increased illumination levels produced by panoptic lamp 711, as will be explained in greater detail below. Trigger controller 752 is in electrical communication with lamp controller 755 that controls panoptic lamp 711, and with solenoid 754 that controls the motion of mirror 731.

A second embodiment of the digital documenting ophthalmoscope 700 is shown in FIG. 7B. Because there are several differences between the two embodiments, the instrument of FIG. 7B is denoted by numeral 702. The digital documenting ophthalmoscope 702 lacks the dot plate 726 present in optical module 720 of digital documenting ophthalmoscope 700. The digital documenting ophthalmoscope 702 comprises a polarizer 744 in imager module 740, which polarizer is lacking in digital documenting ophthalmoscope 700.

Polarizers 715, 734 and 744 are all linear polarizers having a polarization axis. Polarizers 715 and 734, and when polarizer 744 is present, polarizers 715 and 744, are adjustable so that the polarization axis of polarizers 734 and 744 can be oriented relative to the polarization axis of polarizer 715 so that the polarization axes can be positioned at any angular relationship from parallel (e.g., no diminution by polarization of propagating light) to perpendicular (e.g., perfect extinction of propagating light). In the embodiment of FIG. 7B, internal glare reflection is eliminated by use of the polarizers 734 and 744.

Instruments according to principles of the invention provide both a live, diagnosable view and a captured documenting image in a single instrument, which may be handheld in some embodiments. The basic architecture of this instrument is similar to the Welch-Allyn Pan-Optic ophthalmoscope. The instrument according to principles of the present invention includes improvements to facilitate the electronic capture of images gathered by the instrument, which electronic capture of images is not provided in the Welch-Allyn Pan-Optic ophthalmoscope. The polarized image embodiment of FIG. 7B provides a polarized view to both the imager and the viewfinder. Polarizer 734 (P2) in the live view is crossed with illumination polarizer 715 (P1), while polarizer 744 (P3) is crossed with polarizer 715 (P1) in the imager view. For imager 742, which in some embodiments is very sensitive in the near IR region, an additional IR filter 743 is added in the imager view to remove residual IR before the illumination reaches the imager 742. The polarizers 715, 734 and 744 provide a considerable amount of glare reduction, which facilitates aiming of the instrument. Use of crossed polarizers can cause a lack of edge definition and tissue surface reflectivity in the image of the retina. In addition, the crossed polarizers reduce the image irradiance by about 50%, although this problem can be mitigated by the use of a lamp boost circuit, described in greater detail below.

The 'Black Dot' embodiment depicted in FIG. 7A eliminates polarizer 744 (P3), thus providing an unpolarized view to the imager, while retaining the polarizer 734 of the viewfinder (eyepiece). Glare reduction in the imager path is provided in part by a dot plate 726, which is an optical surface with a small black dot in the center to block internal reflections of the illumination system. Glare external to the instrument (primarily corneal and scleral glare) is not filtered by this approach, which is one reason why the viewfinder is still polarized. This external glare is minimized by proper alignment of the instrument 700 to the patient's eye 770. The optical viewfinder is used to properly align the instrument 700 and then capture the unpolarized image. It is possible to incorporate a glare sensor (not shown in FIG. 7A) that senses excessive glare into the imager path. Excessive glare degrades the captured image. The glare sensor provides a feedback signal that causes a status signal to be displayed to the operator of the instrument, such as with a red LED for 'image outside acceptable parameters' and a green LED for 'OK to capture'. The embodiment of FIG. 7A has the advantage of an improvement of edge definition and tissue surface reflectivity in the image of the retina, compared to a polarized image. In addition, the irradiance of the unpolarized image is about 50% higher than the polarized image.

In both embodiments, a movable mirror 731 is provided to direct all of the returning light rays to either the eyepiece or the imager. This ensures that each path receives sufficient light. In embodiments where sufficient light is available through the return path, a beam splitter can be used in place of the mirror 731, to provide a simultaneous view to both the eyepiece and the imager.

In some embodiments, a 'boost' circuit is provided to increase image irradiance. When the operator wishes to capture an image, the trigger 753 is activated. The default position of the mirror 731 is such that illumination passes to the eyepiece 733. Operation of the trigger 753 causes the solenoid 754 to move the mirror to position 731' to send the light rays to the imager 742 and to prevent illumination from reaching the operator's eye 735. In parallel, the trigger 753 activates a 'boost' circuit, which momentarily increases the output of the lamp 711, while the imager 742 is exposed. The lamp 711 is returned to its previous 'normal' output level when the mirror 731 is in position to direct illumination to the eye 735 of the operator. This gives the captured image additional "brightness", but without the drawbacks of a conventional flash lamp illumination system.

Some additional features that can be incorporated in various embodiments of the digital documenting ophthalmoscope according to the invention include the following.

An external fixation target, such as a target on a LED display presented to an eye 770 of a patient, may be provided at an optimal gazing angle for corneal glare control. By holding the eye in a particular gazing angle, the glare reflection from an illumination source can be reduced or eliminated. This fixation target can be any convenient target, such as a picture, a "bulls-eye," an "X" or a visible LED. The fixation target causes the eye to avoid moving, accordingly easing the process of capturing high quality digital images.

A mechanical stabilizer, such as a forehead rest, a browrest, a chinrest, or a device that holds a facial surface in a particular location, can be provided to minimize motions of the head and eye 770 of a patient, and thereby improve control of blur caused by motion.

The apparatus can include a magnifier over a live view image projected on a screen or mirror for control of accommodation of the eye of the operator of the instrument. One can reduce instrument myopia, or tendency toward accommodation of an out-of-focus image by a human viewer, by providing a screen, such as a partially frosted glass or other transparent material or a mirror surface and a magnifier with which the operator can view an image that falls on the partially frosted or mirror surface. In another embodiment, one can present to the eye of an operator of the instrument an image that represents the image that is presented to the imaging device, so that the operator can judge whether proper focus has been achieved. In other embodiments, an autofocus system can be provided to automatically bring the image presented to the imager into focus.

In another embodiment, the apparatus can include a SLR mechanism with dual mirror/window function for real-time observation of a patient's eye 770 by the imager and corneal glare/alignment assessment through a feedback loop from the imager to the live view observed by the instrument operator. The window can provide optical signals to the imager even when much of the light passes through the window and reaches the operator's eye 735. When proper alignment, focus and/or glare reduction is attained, the operator can receive a signal, such as an image of an LED, when one sees visual cues as to the camera's operational state when looking through the viewfinder of a SLR camera.

In some embodiments, the ophthalmoscope can comprise an alignment control using IR light projected onto the patient's cornea and a feedback loop from the imager to the true color live view seen by the operator. The imager detects the IR light reflection, and the apparatus can deduce from the size and/or arrangement of the reflected light image (for example, by observing the number of illuminated pixels and their relative locations) whether the image is in focus and/or a distance to a surface of a patient's eye 770. A signal can be provided to the operator to inform the operator of the status of focus.

In some embodiments, the ophthalmoscope can additionally comprise a feedback loop between the imager and the live view provided to the operator to inform the operator about such features as alignment and glare via LED indicators.

In some embodiments, the ophthalmoscope can include an optional capability of boosting the illumination output with maintenance of a constant spectral envelope. Various options that are possible include using multiple lamps or LED arrays and changing the number of operating units or their intensity, use of an electro-optic shutter to control the amount of illumination impinging on the eye, and boosting the operating point of a single source with constant spectral envelope in the normal and boosted illumination modes.

In some embodiments, the ophthalmoscope includes parfocality/accommodation control. This can be accomplished by any of several methods, such as use of a negative one diopter ("−1D") calibration offset, use of an autofocus imager mechanism, or use of two-step focus setting.

As has been alluded to earlier, the ophthalmoscope can comprise a polarizer in the image path, which polarizer can be adjusted to have an angular relationship with the illumination polarizer varying from parallelism (zero degree difference between the optical axes of the polarizers) to crossed polarizers (e.g., 90 degree difference between the optical axes of the polarizers), or any intermediate value.

While the "true color live view" of the eye 770 of the patient is the "gold standard" today for examination, in the future it may be reasonable to have a display, such as a CRT, flat panel display, or LCD, which display is provided for use by the operator in viewing the eye 770 of the patient. One benefit of such a display may be elimination of accommodation by the eye of the operator.

In some embodiments, different options for corneal glare control can be included and used in ophthalmoscopes of the invention. The options include use of a large working distance (approx. 30 mm) combined with reduced field of view (FOV) (e.g., 16 to 17 deg.); the use of multiple field stops; the use of a "capture many" mode; the use of a polarizer switch in the imager path; the use of an external fixation target, such as one on a swinging arm; the use of a feedback loop from the imager and the live-view; and the use of digital image processing for removal of glare based on sets of images recorded at different polarization vectors.

Figure 8A:
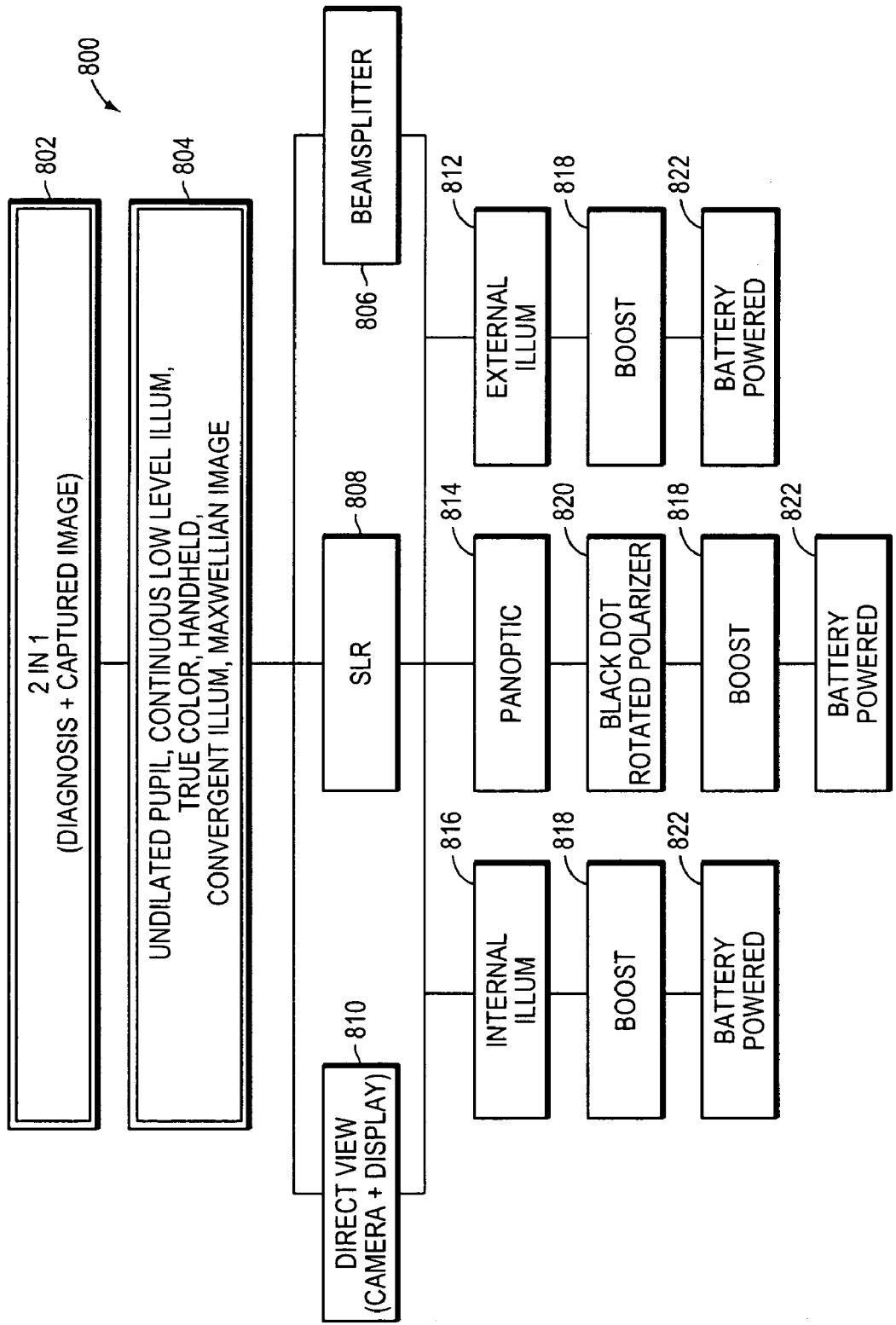
FIG. 8A is a schematic diagram that shows how the elements of a plurality of embodiments of digital documenting ophthalmoscopes are specified and how they cooperate, according to principles of the invention.

FIG. 8A is a schematic diagram 800 that shows how the elements of a plurality of embodiments of digital documenting ophthalmoscopes are specified and how they cooperate. The schematic diagram 800 can be understood as a flow chart for selecting components for use in an apparatus according to the invention, and can also be understood as outlining the operation of such an apparatus as regards the cooperation of the various included components. As indicated at box 802, an apparatus according to the invention will provide at least two capabilities, including diagnostic capability and image capture capability. As As indicated in box 804, any of several configurations can be employed, individually or in combination, including configurations that operate by making observations through an undilated pupil, configurations that employ continuous low level illumination, configurations that provide true color observations, configurations that provide handheld operation, configurations that employ convergent illumination, and configurations that provide a Maxwellian image using a Maxwellian view system. In various embodiments, at least one of the illumination and viewing systems of the device are configured to produce a true color view of the retina suitable for diagnosis. At boxes 806, 808, and 810, one of three viewing regimes is selected as a particular viewing configuration for a particular embodiment of an instrument of the invention. The three alternative viewing regimes are a beamsplitter configuration as indicated at box 806, a single lens reflex ("SLR") configuration as indicated at box 808, and a direct view configuration, for example using a camera and display, as indicated at box 810.

The configurations of instruments according to principles of the invention can further include optical elements as indicated in boxes 812, 814, 816, 818, 820 and 822. In some embodiments, an external illumination source is used, as indicated at box 812. In some embodiments, a PanOptic configuration is used, as indicated at box 814. In the instance that a PanOptic configuration is used, in some embodiments a black dot rotated polarizer is also used, as indicated by box 820. In some embodiment, the instrument comprises an internal illumination source, as indicated at box 816. In each of the internal illumination 816, external illumination 812, and PanOptic 814 configurations, the instrument can further comprise a boost module 818, and can comprise a battery 822 for provision of electrical power under handheld and/or untethered operation, such as an internal battery, with or without a recharging capability.

Figure 8B:
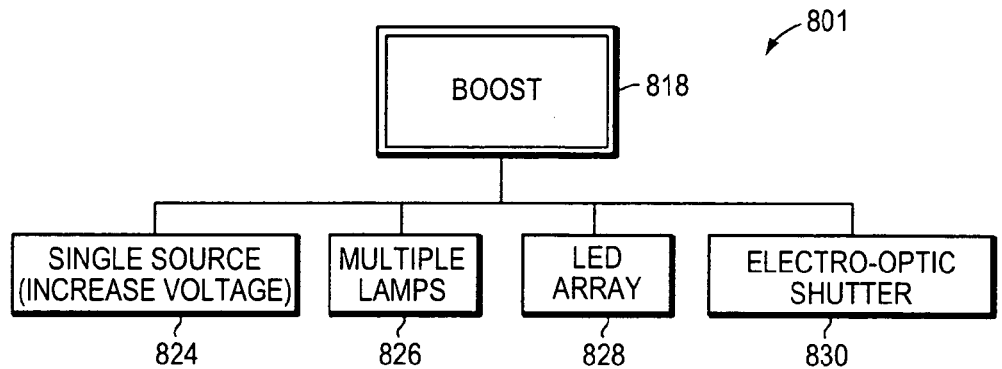
FIG. 8B is a schematic diagram showing alternative embodiments of a boost component, according to principles of the invention.

FIG. 8B is a schematic diagram 801 showing alternative embodiments of a boost module 818 or component. The boost module 818 is provided to increase an illumination capability so as to permit appropriate operation in shorter time periods than would be possible without the boost module 818, as has been described hereinabove. In any instance, due care to assure the safety of a patient and of an operator of the apparatus is exercised, by any or all of provision of limits on the boost module as to power and duration, and provision of limits on exposure of an operator to undesirable illumination and/or power levels. Limits can be implemented in electrical design, for example through use of control circuits, and through mechanical design, such as use of shielding as may be necessary. Embodiments of the boost module 818 and its implementation include increasing an operating voltage of a single source of illumination (whether one or more sources are present) as illustrated by box 824, provision and use of multiple illumination sources such as lamps as indicated by box 826, provision and use of an light emitting diode ("LED") array as indicated by box 828, and use of an electro-optic shutter to control amount and timing of illumination as indicated by box 830. In some instances, combinations of the various embodiments of boost components can be combined, for example using multiple lamps 826 with an electro-optic shutter 830.

Figure 8D:
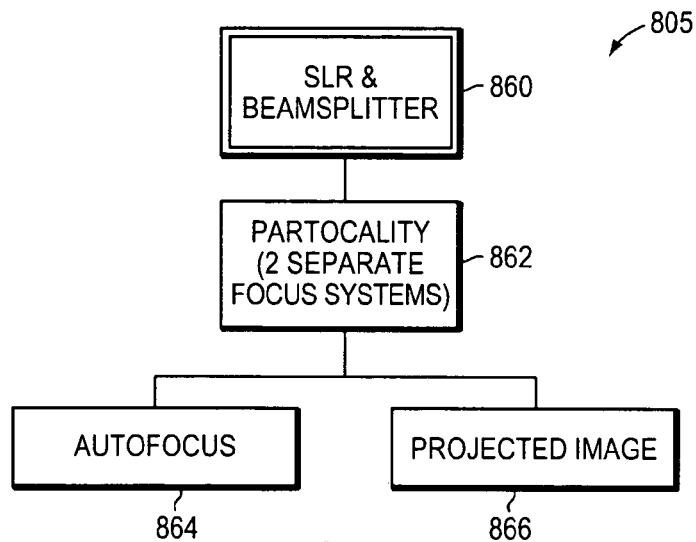
FIG. 8D is a schematic diagram showing alternative embodiments of optical trains that can be employed in instruments designed using principles of the invention.
Figure 8E:
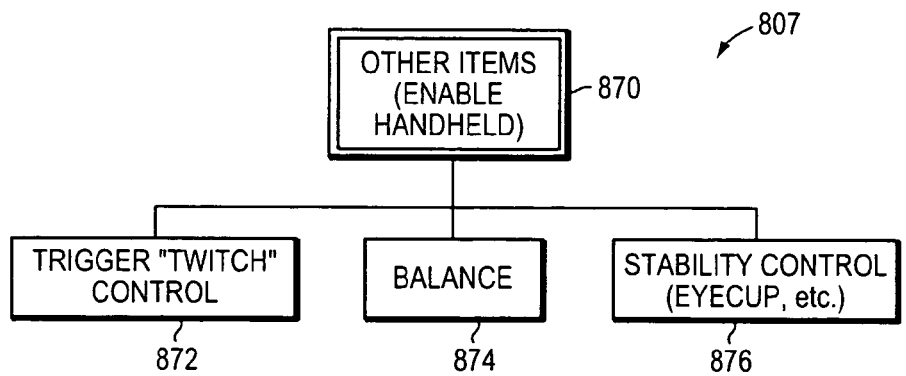
FIG. 8E is a schematic diagram showing additional items of hardware that can be employed in instruments designed using principles of the invention.
Figure 8C:
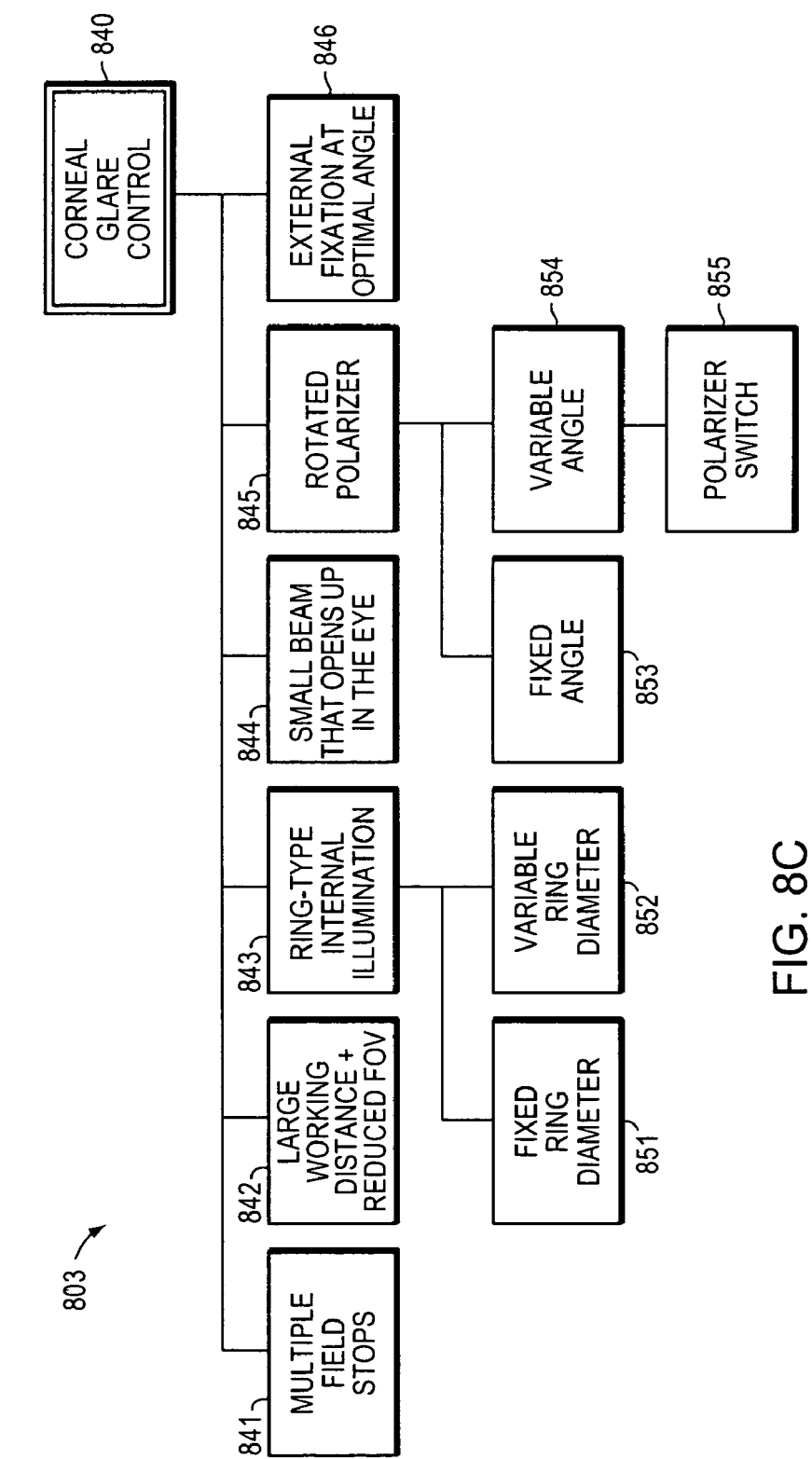
FIG. 8C is a schematic diagram showing alternative embodiments of a corneal glare control component, according to principles of the invention.

FIG. 8C is a schematic diagram 803 showing alternative embodiments of a corneal glare control component 840. It is recognized that the features of glare control and image quality may at times provide mutual constraints, so that improvement in one feature may cause a degradation or a limitation of the ultimately attainable extent of the other feature. Glare control can be implemented using any of a plurality of approaches and apparatus providing suitable characteristics therefor. In FIG. 8C, there are at least ten different approaches indicated. These include: the provision and use of multiple field stops as indicated at box 841; the use of a large working distance and a reduced field of view ("FOV") as indicated at box 842; the provision of ring-type internal illumination, for example with a ring-shaped internal light source, as indicated at box 843; the use of a small beam that expands (or "opens up") within the eye under observation, using a suitably focused light source, as indicated at box 844; the provision and use of a polarizer that is rotated relative to a surface or another polarizer, as indicated at box 845; the use of an external fixation device to cause the eye under test to be fixated at a preferred, and in some circumstances, an optimal angle to avoid glare, as indicated in box 646. Some of the enumerated techniques and associated apparatus are amenable to being performed (and provided) in alternative ways. For example, the ring-type internal illuminator 843 that provides ring-type internal illumination can be accomplished using either a ring having fixed diameter, or a ring having variable diameter, as indicated respectively at boxes 851 and 852. The selection and variation of a diameter of an illumination can be accomplished using any of lenses, irises, and optical stops, for example. Different types of rotated polarizers 845 can be provided with fixed angle polarizers 853, variable angle polarizers 854, and one or more polarizer switches 855, for example.

FIG. 8D is a schematic diagram 805 showing alternative embodiments of optical trains that can be employed in instruments that use principles of the invention. As indicated at box 860, the apparatus can use and SLR and a beamsplitter. At box 862, the apparatus is indicated to provide parfocality, that is, that the object being viewed is in focus when either of two or more objective lenses are interchanged. Here, the SLR and beamsplitter systems have two separate focusing systems so that correct focus for each can be maintained. In the boxes 864 and 866, respectively, autofocus apparatus and projected image apparatus are indicated.

FIG. 8E is a schematic diagram 807 showing additional items of hardware that can be employed in instruments designed using principles of the invention. Box 870 indicates generally that other items of hardware can be provided to enable instruments of the invention to be operated in handheld configuration. One item, indicated at box 872, is a control for a trigger for operating the instrument to eliminate "twitch," or an inappropriate trigger response. Another feature, indicated at box 874, is mechanical balance of the apparatus, so that a user can operate the instrument in handheld mode without undue effort, or without requiring undue strength to maintain the apparatus in a desired orientation. Yet a third feature is stability control, which generally relates to maintaining the instrument in a stable position and orientation with respect to an eye of a patient, such as the provision of an eyecup, a chin rest, a forehead rest, and other mechanical parts that assist in maintaining the correct position and orientation relative to an eye.

Many functions of electrical and electronic apparatus can be implemented in hardware (for example, hard-wired logic), in software (for example, logic encoded in a program operating on a general purpose processor), and in firmware (for example, logic encoded in a non-volatile memory that is invoked for operation on a processor as required). The present invention contemplates the substitution of one implementation of hardware, firmware and software for another implementation of the equivalent functionality using a different one of hardware, firmware and software. To the extent that an implementation can be represented mathematically by a transfer function, that is, a specified response is generated at an output terminal for a specific excitation applied to an input terminal of a "black box" exhibiting the transfer function, any implementation of the transfer function, including any combination of hardware, firmware and software implementations of portions or segments of the transfer function, is contemplated herein.

While the present invention has been particularly shown and described with reference to the structure and methods disclosed herein and as illustrated in the drawings, it is not confined to the details set forth and this invention is intended to cover any modifications and changes as may come within the scope and spirit of the following claims.

What is claimed is:

1. A hand held digital documenting ophthalmoscope, comprising:
    an illumination module for providing continuous, convergent illumination;
    an optical module configured to direct at least a portion of said illumination to an eye and to communicate return illumination from said eye through an undilated pupil of said eye, said at least a portion of said illumination directed toward said eye having an intensity below a safety limit, said optical module comprising a Maxwellian view system;
    a viewing module having an eyepiece configured to provide a true color live view to an operator of at least a portion of said eye using said return illumination;
    an electronic imager module having an imager for capturing an image of at least a portion of said eye using said return illumination;
    a mirror having a first state to provide said true color live view of at least a portion of the eye and a second state to provide said image of at least a portion of said eye;
    an illumination control apparatus configured to direct said return illumination from said eye in part to said viewing module and in part to said electronic imager module wherein said illumination control apparatus is configured to control in serial temporal fashion said return illumination directed in part to said viewing module and in part to said electronic imager module, such that direct viewing occurs during a first time interval and electronic imaging occurs during a second time interval, wherein said first and second time intervals do not substantially overlap and in which an integration time of said electronic imager module is selectively adjustable; and
    a dot plate glare removal apparatus.

2. The digital documenting ophthalmoscope of claim 1, wherein said illumination control apparatus is a selected one of a mirror and a shutter.

3. The digital documenting ophthalmoscope of claim 2, wherein said mirror is a selected one of a movable mirror and an electronically controllable mirror.

4. The digital ophthalmoscope of claim 1, wherein an integration time interval of said electronic imager module is adjusted to be different than that of the viewing time interval.

5. The digital documenting ophthalmoscope of claim 1, wherein said dot plate glare removal apparatus includes a polarizer and a dot plate.

6. The digital documenting ophthalmoscope of claim 1, wherein a field of view of at least 10 degrees is accessible for a selected one of a true color live view and an electronic image.

7. The digital documenting ophthalmoscope of claim 1, wherein at least one of said illumination module and said optical module comprise a reconfigurable illumination system wherein an illumination angle is adjustable.

8. A method of obtaining information about at least a portion of an eye of a patient, comprising the steps of:
    providing a hand held digital documenting ophthalmoscope, said hand held digital documenting ophthalmoscope comprising:
    an illumination module for providing continuous, convergent illumination;
    an optical module configured to direct at least a portion of said illumination to an eye and to communicate return illumination from said eye through an undilated pupil of said eye, said at least a portion of said illumination directed toward said eye having an intensity below a safety limit, said optical module comprising a Maxwellian view system;
    a viewing module having an eyepiece configured to provide a live view by an operator of at least a portion of said eye using said return illumination, said live view being a true color live view suitable for diagnosis;
    an electronic imager module having an imager for capturing an image of at least a portion of said eye using said return illumination;
    a dot plate glare removal apparatus; and
    a mirror having a first state to provide said true color live view of at least a portion of the eye and a second state to provide said image of at least a portion of said eye;
    illuminating at least a portion of said eye with illumination from said illumination module, said illumination passing through said optical module in at least one direction;
    controlling said state of said mirror; and
    depending on said state of said mirror, providing a selected one of a true color live view of at least a portion of said eye and an image of at least a portion of said eye;
    whereby information about at least a portion of said eye is obtained, said method further comprising the step of directing said return illumination from said eye in part to said viewing module and in part to said electronic imager module wherein the step of directing said return illumination from said eye in part to said viewing module and in part to said electronic imager module comprises providing a direct view during a first time interval and providing electronic imaging during a second time interval, wherein said first and second time intervals do not substantially overlap, said method further comprising the step of selectively adjusting an integration time of said electronic imager module.

9. The method of claim 8, further comprising the step of removing glare from a selected one of said true color live view of said portion of said eye and said image of said portion of said eye.

10. A hand held digital documenting ophthalmoscope, comprising:

an illumination module for providing continuous, convergent illumination;

an optical module configured to direct at least a portion of said illumination to an eye and to communicate return illumination from said eye through an undilated pupil of said eye, said at least a portion of said illumination directed toward said eye having an intensity below a safety limit, said optical module comprising a Maxwellian view system;

a viewing module having am eyepiece configured to provide a true color live view to an operator of at least a portion of said eye using said return illumination;

an electronic imager module having an imager for capturing an image of at least a portion of said eye using said return illumination;

a mirror having a first state to provide said true color live view of at least a portion of the eye and a second state to provide said image of at least a portion of said eye; and a dot plate glare removal apparatus for removing glare from a selected one of said true color live view of said portion of said eye and said image of said portion of said eye.

11. The digital documenting ophthalmoscope of claim 10, wherein said dot plate glare apparatus includes at least one polarizer and a dot plate.

12. A hand held digital documenting ophthalmoscope, comprising:

an optical module configured to direct at least a portion of said illumination to an eye and to communicate return illumination from said eye through an undilated pupil of said eye, said at least a portion of said illumination directed toward said eye having an intensity below a safety limit, said optical module comprising a Maxwellian view system;

a viewing module having an eyepiece configured to provide a true color live view to an operator of at least a portion of said eye using said return illumination;

an electronic imager module having an imager for capturing an image of at least a portion of said eye using said return illumination; and a mirror having a first state to provide said true color live view of at least a portion of the eye and a second state to provide said image of at least a portion of said eye wherein at least one of said illumination module and said optical module comprise a reconfigurable illumination system wherein an illumination angle is adjustable through interposition of at least one replaceable lens module of said system.

13. A method of obtaining information about at least a portion of an eye of a patient, comprising the steps of:

providing a hand held digital documenting ophthalmoscope, said hand held digital documenting ophthalmoscope comprising:

an illumination module for providing continuous, convergent illumination;

an optical module configured to direct at least a portion of said illumination to an eye and to communicate return illumination from said eye through an undilated pupil of said eye, said at least a portion of said illumination directed toward said eye having an intensity below a safety limit, said optical module comprising a Maxwellian view system;

a viewing module having an eyepiece configured to provide a live view by an operator of at least a portion of said eye using said return illumination, said live view being a true color live view suitable for diagnosis;

an electronic imager module having an imager for capturing an image of at least a portion of said eye using said return illumination; and a mirror having a first state to provide said true color live view of at least a portion of the eye and a second state to provide said image of at least a portion of said eye;

illuminating at least a portion of said eye with illumination from said illumination module, said illumination passing through said optical module in at least one direction;

controlling said state of said mirror; and depending on said state of said mirror, providing a selected one of a true color live view of at least a portion of said eye and an image of at least a portion of said eye;

whereby information about at least a portion of said eye is obtained and in which at least one of said illumination module and said optical module comprise a reconfigurable illumination system wherein an illumination angle is adjustable by interposing at least one replaceable lens module.

* * * * *